US006869766B2

(12) United States Patent
Reue et al.

(10) Patent No.: US 6,869,766 B2
(45) Date of Patent: Mar. 22, 2005

(54) GENE ASSOCIATED WITH REGULATION OF ADIPOSITY AND INSULIN RESPONSE

(75) Inventors: Karen Reue, Torrance, CA (US); Miklós Péterfy, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/028,056

(22) Filed: Dec. 19, 2001

(65) Prior Publication Data

US 2002/0152483 A1 Oct. 17, 2002

Related U.S. Application Data

(60) Provisional application No. 60/257,772, filed on Dec. 22, 2000.

(51) Int. Cl.[7] .......................... C12Q 1/68; C12P 19/34; C12N 5/02; C07H 21/04

(52) U.S. Cl. ........................ 435/6; 435/91.1; 435/91.2; 435/325; 536/23.1; 536/24.3; 536/24.32; 536/24.33

(58) Field of Search ........................... 435/6, 91.2, 7.1, 435/173.6; 536/23.1, 24.32, 24.33

(56) References Cited

U.S. PATENT DOCUMENTS 5,476,926 A 12/1995 Speigelman et al.
5,698,389 A 12/1997 de la Brousse et al.
5,723,115 A 3/1998 Serrero
5,756,467 A 5/1998 Kagawa et al.
5,776,906 A 7/1998 Sekiya
5,827,740 A 10/1998 Pittenger
5,855,917 A 1/1999 Cook et al.
5,935,810 A 8/1999 Freidman et al.
6,232,066 B1 * 5/2001 Felder et al. .................. 435/6

FOREIGN PATENT DOCUMENTS

WO WO 93/14109 A1 7/1993
WO WO 99/29725 A1 6/1999
WO WO 99/45135 A1 9/1999
WO WO 99/51740 A2 10/1999
WO WO 00/28444 A1 5/2000

OTHER PUBLICATIONS

Klingenspor et al. Altered Gene expression pattern in the fatty liver dystrophy mouse reveals impaired insulin–mediated cytoskeleton dynamics. vol. 274, No. 33, pp. 23078–23084, Aug. 1999.*

Ailhaud et al. (1992) "Cellular and Molecular Aspects of Adipose Tissue Development" *Ann. Rev. Nutr.* 12: 207–233.

Cao and Hegele (2000) "Nuclear lamin A/C R482Q mutation in Canadian kindreds with Dunnigan–type familial partial lipodystrophy" *Hum. Mol. Genet.* 9: 109–112.

Comuzzie et al. (1997) "A major quantitative trait locus determining serum leptin levels and fat mass is located on human chromosome 2" *Nature Genet.* 15: 273–275.

Dörfler et al. (1993) "Lipoatrophic diabetes" *Clin. Investig.* 71: 264–269.

Garg (2000) "Gender Differences in the Prevalence of Metabolic Complications in Familiar Partial Lipodystrophy (Dunnigan Variety)" *J. Clin. Endocrinol. Metab.* 85: 1776–1782.

Hager et al. (1998) "A genome–wide scan for human obesity genes reveals a major susceptibility locus on chromosome 10" *Nature Genet.* 20: 304–308.

Klingenspor et al., (1999) "Altered Gene Expression Pattern in the Fatty Liver Dystrophy Mouse Reveals Impaired Insulin–mediated Cytoskeleton Dynamics" *J. Biol. Chem.* 274: 23078–23084.

Langner et al. (1989) "The Fatty Liver Dystophy (fld) Mutation" *J. Biol. Chem.* 264: 7994–8003.

Langner et al. (1991) "Characterization of the Peripheral Neuropathy in Neonatal and Adult Mice That Are Homozygous for the Fatty Liver Dystophy (fld) Mutation" *J. Biol. Chem.* 266: 11955–11964.

Péterfy et al. (1999) "Genetic, Physical, and Transcript Map of the fld Region on Mouse Chromosome 12" *Genomics* 62: 436–444.

Rehnmark et al. (1998) "The fatty liver dystrophy mutant mouse: microvesicular steatosis associated with altered expression levels of peroxisome proliferator–regulated proteins" *J. Lipid Res.* 39: 2209–2217.

Rotimi et al. (1999) "The Quantitative Trait Locus on Chromosome 2 for Serum Leptin Levels Is Confirmed in African–Americans" *Diabetes* 48: 643–644.

Seip and Trygstad (1996) "Generalized lipodystrophy, congenital and acquired (lipoatrophy)" *Acta Paediatr. Scand. Suppl.* 413: 2–28.

Senior and Gellis (1964) "The Syndromes of Total Lipodystrophy and of Partial Lipodystrophy" *Pediatrics* 33: 593–612.

Shackleton et al. (2000) "*LMNA*, encoding lamin A/C, is mutated in partial lipodystophy" *Nature Genet.* 24: 153–156.

Shimomura et al. (1998) "Insulin resistance and diabetes mellitus in transgenic mice expressing nuclear SREBP–1c in adipose tissue: model for congenital generalized lipodystrophy" *Genes. Dev.* 12: 3182–3194.

Shimomura et al. (1999) "Congenital generalized lipodystrophy (CGL) is a rate autosomal recessive disorder characterized by a paucity of adipose (fat) tissue which is evident at birth and . . . " *Nature* 401: 73–76.

* cited by examiner

*Primary Examiner*—Kenneth R. Horlick
*Assistant Examiner*—Cynthia Wilder
(74) *Attorney, Agent, or Firm*—Quine I. D. Law Group, PC.

(57) ABSTRACT

This invention pertains to the identification and isolation of a gene implicated in the fatty liver dystrophy (fld) phenotype. Mouse and human forms of the novel gene, designated herein as Lpin1/LPIN1 (mouse and human genes, respectively), are identified. This invention additionally provides methods of screening for agents that alter adipose tissue development. The methods involve contacting a cell containing a Lpin1 gene with a test agent; and detecting a change in the expression or activity of a Lpin1 gene product, where a difference in the expression or activity of Lpin1 in the contacted cell indicates that the agent alters or is likely to alter adipose tissue development. Also provided are methods of identifying Lpin1 mutations, and methods of mitigating symptoms of lipodystrophy, obesity, diabetes, atherosclerosis and related pathologies.

17 Claims, 9 Drawing Sheets

Fig. 1A
Fig. 1B
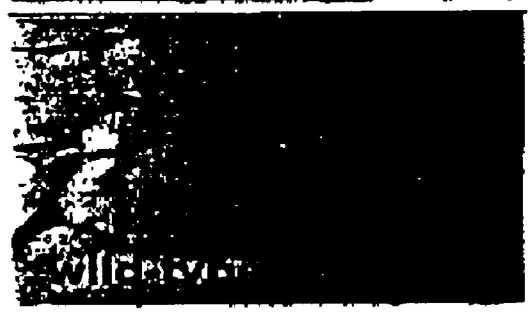
Fig. 1C
Fig. 1D
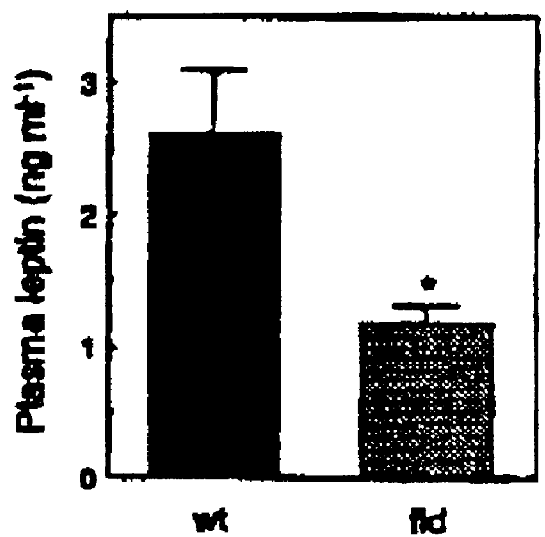

Fig. 3A
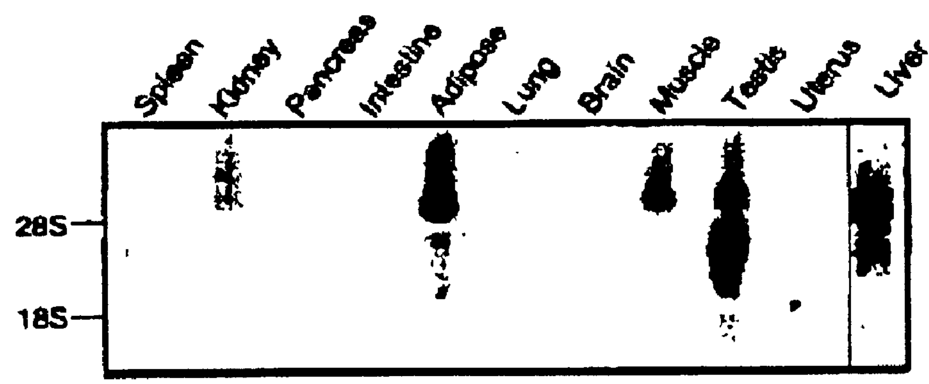
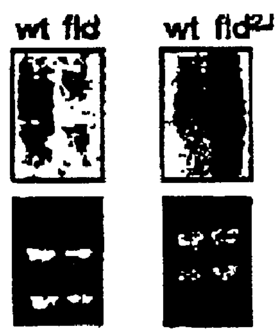
Fig. 3B
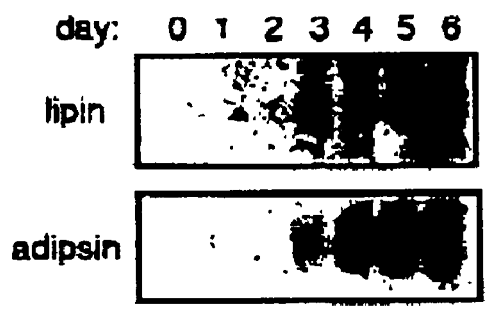
Fig. 3C

Fig. 4A
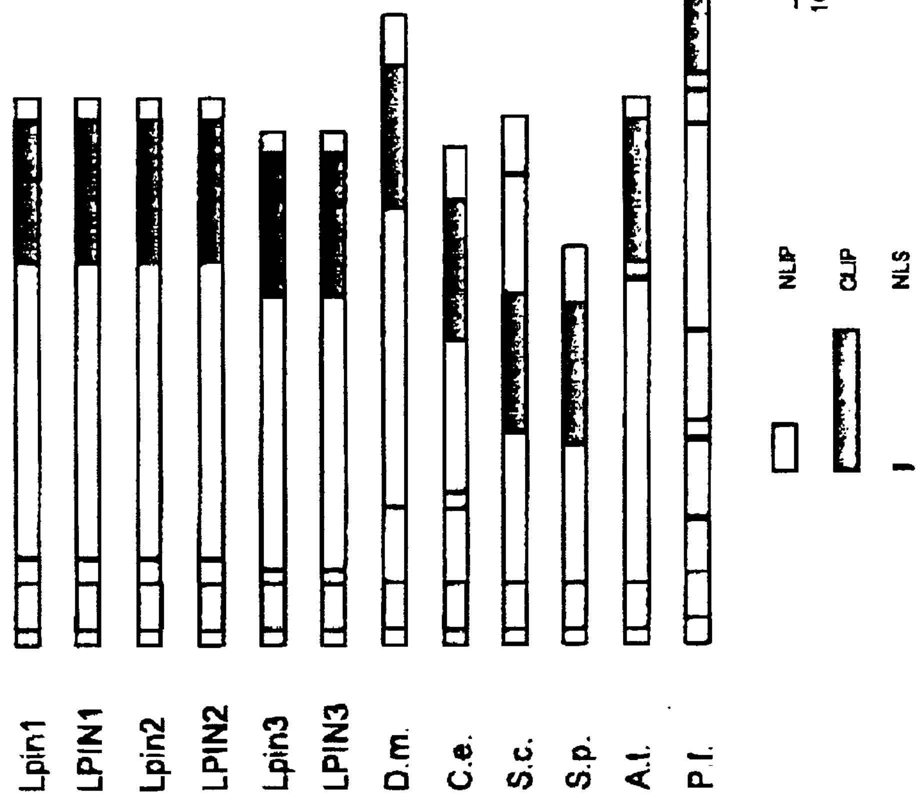
Fig. 4B
pEGFP
pEGFP-Lpin1
GFP
Hoechst
Fig. 4C
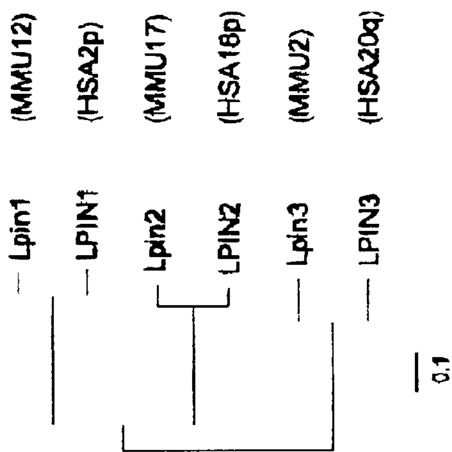

*Fig. 5A*
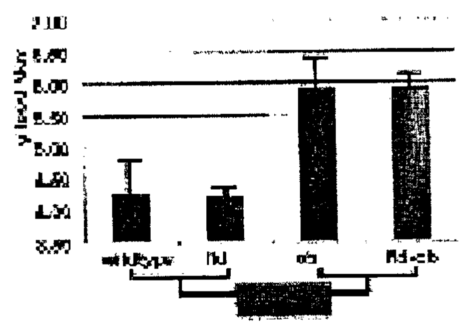
*Fig. 5B*
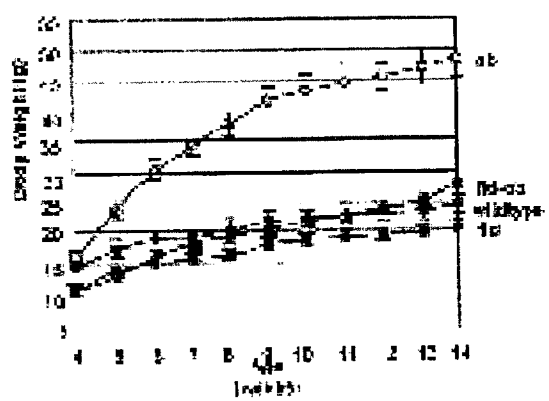
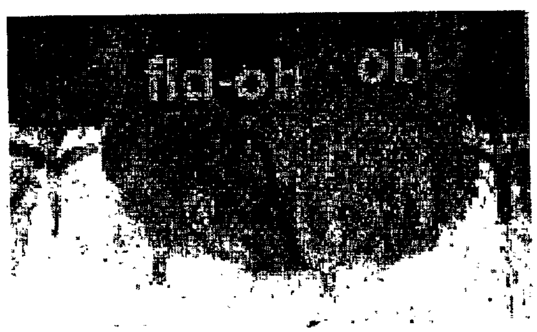
*Fig. 5C*

GENE ASSOCIATED WITH REGULATION OF ADIPOSITY AND INSULIN RESPONSE

CROSS-REFERENCE TO RELATED APPLICATIONS

This application claims priority to and benefit of U.S. Ser. No. 60/257,772, filed on 22 Dec. 2000, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support by the Veterans Administration, and under Grant No: HL28481, awarded by the National Institutes of Health. The Government of the United States of America may have certain rights in this invention.

FIELD OF THE INVENTION

This invention pertains to the field of adipose tissue development and fat metabolism. In particular, this invention pertains to the identification of a gene implicated in the development of lipodystrophy.

BACKGROUND OF THE INVENTION

Considerable work has been performed in the field of adipocyte differentiation in an effort to delineate the specific factors and processes involved. Fat cells or adipocytes are a specialized cell type that synthesizes and stores fat (triglycerides) in periods of nutritional abundance, and hydrolyze these fats when needed to meet demand for energy. The size and distribution of adipose tissue stores in humans and animals clearly influences metabolism and the development of diseases including, but not limited to obesity and diabetes.

The development of mature adipocytes from precursor cells, a process known as differentiation has been widely studied. Most adipocyte differentiation occurs shortly before or after birth, but further differentiation can occur at any time during life in response to various hormonal and nutritional signals.

A few key proteins that are expressed early in the process of differentiation and are required for adipocyte development have been identified. These include the nuclear hormone receptor peroxisome proliferator-activated receptor γ (PPARγ) and CAAT/enhancer binding protein α (C/EBPα). It is known that these proteins function as transcription activators to induce the expression of genes required for conversion of precursor cells into mature adipocytes. However, many aspects of the regulation and function of these proteins have not been delineated. It is known that proteins such as PPARγ and C/EBPα function in complexes with other protein factors, known as co-activators, to effect transcription.

SUMMARY OF THE INVENTION

This invention pertains to the identification and isolation of a gene implicated in the fatty liver dystrophy (fld) phenotype. In particular, this invention relates to the isolation of both mouse and human forms of a novel gene (designated herein as Lpin1 and LPIN1, respectively), that is rearranged in the fld genome leading to a null allele. An fld mutant animal exhibits an array of abnormalities in lipid and glucose metabolism. In particular, as fld animals age, they exhibit reduced weight gain and adipose tissue mass, develop glucose intolerance and hyperinsulinemia, and are more susceptible to diet-induced atherosclerosis. Without being bound by a particular theory, it is believed that a Lpin1 gene product may interact with proteins such as PPARγ and C/EBPα, or other proteins involved in adipocyte differentiation.

In one embodiment, this invention provides a method of screening for an agent that alters adipose tissue development. The method involves contacting a cell comprising a Lpin1 gene with a test agent; and detecting a change in the expression or activity of a Lpin1 gene product as compared to the expression or activity of a Lpin1 gene product in a cell that is contacted with the test agent at a lower concentration, where a difference in the expression or activity of lipin in the contacted cell and the cell that is contacted with the lower concentration indicates that the test agent alters adipose tissue development. In preferred embodiments, the lower concentration is the absence of the test agent. In certain embodiments, the of Lpin1 gene product is detected by detecting Lpin1 mRNA in the sample, e.g., by hybridizing said mRNA to a probe that specifically hybridizes to a Lpin1 nucleic acid. Preferred hybridization assays include, but are not limited to Northern blot, Southern blot using DNA derived from the Lpin1 RNA, a array hybridization, affinity chromatography, and in situ hybridization. In one particularly preferred embodiment, the assay utilizes a Lpin1 probe that is a member of a plurality of probes that forms an array of probes (e.g. a high-density array). In certain other nucleic acid-based assays, the Lpin1 mRNA is measured using a nucleic acid amplification reaction.

In other embodiments, the amount of Lpin1 gene product is detected by detecting the level of a lipin protein in the biological sample, e.g. via a method selected from the group consisting of capillary electrophoresis, Western blot, mass spectroscopy, ELISA, immunochromatography, immunohistochemistry, and the like. The cells used in these assays can be cells in vivo in an organism or can be ex vivo (e.g. cultured cells). In certain embodiments, the test agent is contacted to an animal comprising a cell containing the Lpin1 nucleic acid or the lipin protein.

This invention also provides methods of prescreening for an agent that alters adipose tissue development. Such methods typically involve contacting a Lpin1 nucleic acid or a lipin protein with a test agent; and detecting specific binding of the test agent to the lipin protein or nucleic acid. The methods can further involve recording test agents that specifically bind to the Lpin1 nucleic acid or protein in a database of candidate agents that alter adipose tissue development. In certain embodiments, the test agent is not an antibody and/or not a protein, and/or not a nucleic acid. Particularly preferred test agents include, but are not limited to small organic molecules. In preferred embodiments, the detecting comprises detecting specific binding of the test agent to the Lpin1 nucleic acid (e.g. via Northern blot, Southern blot using DNA derived from a Lpin1 RNA, array hybridization, affinity chromatography, in situ hybridization, and the like). In other embodiments, the detecting comprises detecting specific binding of the test agent to lipin protein (e.g. via capillary electrophoresis, Western blot, mass spectroscopy, ELISA, immunochromatography, immunohistochemistry, and the like). In certain embodiments, the test agent is contacted directly to the Lpin1 nucleic acid or to the lipin protein, while in other embodiments, the test agent is contacted to a cell containing (comprising) the Lpin1 nucleic acid or the lipin protein. The cells can be in vivo or ex vivo, but particularly preferred cells are ex vivo (e.g. cultured fresh cells or cell lines). In certain embodiments, the test agent is contacted to an animal comprising a cell containing (comprising) the Lpin1 nucleic acid or the lipin protein.

This invention also provides an isolated nucleic acid comprising a nucleic acid selected from the group consisting of: a nucleic acid encoding a polypeptide selected from the group consisting of human lipin 1A (SEQ ID NO:3), mouse lipin 1A (SEQ ID NO:4), and mouse lipin 1B (SEQ ID NO:5); a nucleic acid that hybridizes to a nucleic acid selected from the group consisting of mouse Lpin1 (SEQ ID NO:1), and human LPIN1 (SEQ ID NO2) under stringent conditions; a nucleic acid having the sequence of a nucleic acid selected from the group consisting of mouse Lpin1 (SEQ ID NO:1), and human LPIN1 (SEQ ID NO2); a nucleic acid that hybridizes to a nucleic acid selected from the group consisting of mouse Lpin1 (SEQ ID NO:1), and human LPIN1 (SEQ ID NO2) under stringent conditions and that encodes an lipin polypeptide; a nucleic acid having the sequence of a nucleic acid amplified using primer 1 (SEQ ID NO:6) and primer 2 (SEQ ID NO:7) using cDNA from mouse cells or tissues as a template; and a nucleic acid having the sequence of a nucleic acid amplified using primer 3 (SEQ ID NO:8) and primer 4 (SEQ ID NO:9) using cDNA from human cells or tissues as a template. Preferred nucleic acids are sufficiently long to hybridize specifically with a Lpin1 nucleic acid. A preferred nucleic acid is at least 15 nucleotides in length. In one particularly preferred embodiment the nucleic acid comprises a mouse Lpin1 (SEQ ID NO:1), and/or a human Lpin1 (SEQ ID NO2).

This invention also provides a comprising a polypeptide encoded by a nucleic acid as described above and herein and/or an antibody that specifically binds such a polypeptide. Particularly preferred polypeptides include lipin polypeptides comprising a polypeptide that comprises an NLIP domain and a CLIP domain.

In still another embodiment, this invention provides a transgenic animal comprising a recombinantly modified Lpin1/LPIN1 gene such that the recombinantly modified gene does not transcribe a functional lipin protein. A preferred transgenic animal is homozygous for the recombinantly modified Lpin1/LPIN1 gene. Certain preferred transgenic animals are chimeric for cells comprising said recombinantly modified Lpin1/LPIN1 gene. Preferred transgenic animals include, felines, canines, equines, largomorphs, murines, mice, rodents, and the like.

This invention provides a method of identifying a predilection to developing one or more symptoms of lipodystrophy, obesity, diabetes, or atherosclerosis (e.g., a methods of identification mutations in the LPIN1 gene). Preferred methods involve obtaining a biological sample from the organism; and detecting a mutation in a Lpin1/LPIN1 gene or gene product from the biological sample. In preferred embodiments, the mutation is an insertion, a deletion, a missense point mutation, a nonsense point mutation, etc. Preferred detection methods include, but are not limited to Southern blot, DNA amplification, comparative genomic hybridization (CGH), immunohistochemistry, cytogenetics, and the like. In other embodiments, the detecting comprises detecting a mutation in a polypeptide, e.g. via capillary electrophoresis, Western blot, mass spectroscopy, ELISA, immunochromatography, immunohistochemistry, and the like.

In still another embodiment, this invention provides a method of identifying a predilection to developing one or more symptoms of lipodystrophy, obesity, diabetes, by detecting alterations in 1 pin expression. Thus the methods preferably involve obtaining a biological sample from the organism; and detecting a LPIN1 gene product wherein a difference in the amount or activity of the LPIN1 gene product from the organism as compared to the LPIN1 gene product from a normal healthy organism indicates that the organism has or is susceptible to lipodystrophy, obesity, diabetes, atherosclerosis, and related pathologies. In preferred embodiments, the amount of LPIN1 gene product is detected by detecting LPIN1 mRNA in the cell (e.g., by hybridizing the mRNA or a nucleic acid derived therefrom to a probe that specifically hybridizes to a LPIN1 nucleic acid). Preferred hybridization methods include, but are not limited to Northern blot, Southern blot using DNA derived from the LPIN1 RNA, array hybridization, affinity chromatography, in situ hybridization, and the like. In certain embodiments, the probe is a member of a plurality of probes that forms an array of probes. In certain embodiments, the level of LPIN1 mRNA is measured using a nucleic acid amplification reaction. The amount of LPIN1 gene product can also be detected by detecting the level of lipin protein in the biological sample (e.g. via Western blot, mass spectroscopy, ELISA, immunochromatography, immunohistochemistry, etc.).

This invention also provides methods of mitigating a symptom of lipodystrohy, obesity, diabetes, atherosclerosis or related pathology. The methods involve modulating the concentration and/or activity of a LPIN1 gene product in a cell of an organism e.g., by upregulating or repressing expression of a heterologous LPIN1 nucleic acid or by upregulating or repressing expression of an endogenous LPIN1 gene. In preferred embodiments, 1 pin expression is upregulated, e.g. by transfecting the cell with a vector (e.g. constitutive, inducible, tissue-specific, etc.) that expresses a lipin protein. Preferred cells are adipocytes.

Definitions.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach,* Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995)

*Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research,* Ed. Y. S. Sanghui and P. Dan Cook. Nucleic acids containing one or more carbocyclic sugars are also included within the definition of nucleic acids (see Jenkins et al. (1995), *Chem. Soc. Rev. pp*169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

As used herein, the term "derived from a nucleic acid" (e.g., an mRNA) refers to a nucleic acid or protein nucleic acid for whose synthesis the referenced nucleic acid or a subsequence thereof has ultimately served as a template. Thus, a cDNA reverse transcribed or RT-PCR'd from an mRNA, an RNA transcribed from that cDNA, a DNA amplified from the cDNA, an RNA transcribed from the amplified DNA, etc., are all derived from the mRNA. In preferred embodiments, detection of such derived products is indicative of the presence and/or abundance of the original nucleic acid in a sample.

A "nucleic acid derived from a Lpin1 gene or cDNA" refers to a nucleic acid whose synthesis the Lpin1 gene or cDNA has ultimately served as a template. Thus, for example, a cDNA reverse transcribed from a Lpin1 mRNA, an RNA transcribed from that cDNA, a DNA amplified from the cDNA, an RNA transcribed from the amplified DNA, etc., are all nucleic acids derived from the Lpin1 gene or cDNA.

A Lpin1 nucleic acid refers to a nucleic acid derived from a Lpin1 gene, mRNA or cDNA, or a nucleic acid having the same sequence as a nucleic acid derived from a 1 pin gene, mRNA or cDNA. A 1 pin nucleic acid also includes fragments of such nucleic acids. In preferred embodiments, the fragments are of sufficient length to uniquely identify them as 1 pin gene mRNA or cDNA subsequences. Preferred fragments are at least 10 nucleotides, more preferably at least 15 nucleotides, still more preferably at last 20 nucleotides, and most preferably at least 25, 50, 100 or 200 nucleotides in length.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann et al. (1993) *Proc. Natl. Acad. Sci. USA,* 90: 547–551), an Fab or (Fab)'2 fragment containing the variable regions and parts of the constant regions, a single-chain antibody and the like (Bird et al. (1988) *Science* 242: 424–426; Huston et al. (1988) *Proc. Nat. Acad. Sci. USA* 85: 5879–5883). The antibody may be of animal (especially mouse or rat) or human origin or may be chimeric (Morrison et al. (1984) *Proc Nat. Acad. Sci. USA* 81: 6851–6855) or humanized (Jones et al. (1986) *Nature* 321: 522–525, and published UK patent application #8707252).

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence of a biomolecule in a heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all, to other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt* 2, *Overview of principles of hybridization and the strategy of nucleic acid probe assays,* Elsevier, NY (Tijssen ). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions, e.g., containing formamide (see, e.g., Sambrook (1989) *Molecular Cloning: A Laboratory Manual* (*2nd ed.*) *Vol.* 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

BRIEF DESCRIPTION OF THE DRAWINGS

FIGS. 1A, 1B, 1C, and 1D illustrate adipose deficiency in fld mutant mice. FIG. 1A: Exposed ventral view of wild-type and fld littermates at 3 months of age showing vastly reduced epididymal adipose tissue in the fld mouse. FIG. 1B and FIG. 1C: Cross sections of epididymal fat pads from wild-type and fld mice, respectively. Tissue was stained with haematoxylin/eosin and viewed at a magnification of 330×. Adipocytes from fld mice appear immature, with small heterogeneous lipid droplets. FIG. 1D: Plasma leptin levels are substantially reduced in fld compared to wild-type (wt) mice. Values represent mean±SD for three mice of each type. Asterisk, P<0.005.

FIG. 2A: Genomic DNA from wild-type (+/+), fld (fdl/fld) and heterozygous (+/fld) mice was restriction digested with HindIII (left panel) or SacI (right panel) and hybridized to probes from the 5' or 3' region of lipin cDNA (see panel c for position of probes in the gene). The fld allele exhibits aberrant hybridization patterns indicating DNA deletion and duplication for the 5' and 3' probes, respectively. FIG. 2B: Genomic DNA from wild-type (w) and fld/fld (f) mice was PCR amplified using primer pairs flanking the regions that are deleted (p1+p2) and duplicated (p3+p4) in the fld mutant allele. PCR products were generated from the wild-type allele with primer pairs p1+p2 and p3+p4, whereas products from the fld allele were only generated when the two forward primers (p1+p3) or the two reverse primers (p2+p4) were paired, confirming an internal gene rearrangement. FIG. 2C: Structure of wild-type and fld alleles of Lpin1. At top, exons are represented as boxes, with filled and open boxes representing coding and non-coding regions, respectively. Below is a schematic diagram of the wild-type allele, where the gene is divided into 5 segments represented by distinctly colored rectangles, with arrowheads indicating orientation. In the rearranged fld allele shown at bottom, the red segment of the wild-type allele containing exons 2 and 3 has been deleted, while the green segment containing most of the coding exons has been inverted (indicated by reverse arrowhead). Moreover, in fld the yellow segment of the wild-type allele containing a portion of the 3'UTR has been both duplicated and inverted. Positions of the probes and primers used in experiments presented in FIGS. 2A and 2B are also indicated. Figure is not drawn to scale. FIG. 2D: Sequence traces showing the Gly84Arg substitution in the $fld^{2J}$ allele. The mutation occurs in the NLIP domain of the protein in a position that is invariably conserved in species ranging from mouse and human to yeast (see asterisk in FIG. 4D).

FIGS. 3A through 3C illustrate lipin mRNA expression. FIG. 3A: Lipin mRNA tissue distribution in wild-type mouse tissues. A partial lipin cDNA probe (exons 1–8) was hybridized to 20 $\mu$g total RNA (all tissues except liver), or 2 $\mu$g poly A+ RNA (liver). FIG. 3B: Aberrant lipin mRNA expression levels in adipose tissue from fld/fld and $fld^{2J}/fld^{2J}$ mice. At left, no full length mRNA was detected in fld tissue; at right, elevated lipin mRNA was detected in $fld^{2J}$ tissue. Ethidium bromide stained RNA is shown below blots to demonstrate equal loading. FIG. 3C: Lipin mRNA induction during 3T3-L1 preadipocyte differentiation. Total RNA (20 $\mu$g) from cultures of 3T3-L1 cells maintained in differentiation medium for 0 to 6 days (see Methods) was hybridized to cDNA for lipin or adipsin.

FIGS. 4A through 4C illustrate evolutionary conservation of the lipin protein family and nuclear localization of lipin. FIG. 4A: Lipin-homologs were identified from mouse, human, *Drosophila melanogaster* (*D.m.*), *Caenorhabditis elegans* (*C.e.*), *Saccharomyces cerevisiae* (*S.c.*), *Schizosaccharomyces pombe* (*S.p.*), *Arabidopsis thaliana* (*A.t.*) and *Plasmodium falciparum* (*P.f.*). Lpin1 (GenBank accession number AAF44296), Lpin2 and Lpin3 sequences were deduced from full-length cDNAs obtained by RACE cloning in this study. The LPIN1 (Q14693), LPIN2 (Q92539), D.m. (AAF59125), C.e. (CAA16154), S.c. (P32567), S.p. (CAB52577), A.t. (AAF23287) and P.f. (CAB10579) protein sequences are based on predictions from EST and genomic sequences. LPIN3 was predicted in this study using the genomic sequence in AL132654. NLIP (blue) and CLIP (green) domains, and predicted nuclear localization signals (red) are indicated. FIG. 4B: 3T3-L1 cells were transfected with pEGFP, a GFP expression vector, or the same vector containing lipin cDNA to produce a lipin-GFP fusion protein. At 48 hr post-transfection, nuclei were stained with the DNA-specific dye Hoechst-33258, and cells were observed in a fluorescent microscope for either GFP (left) or Hoechst fluorescence (right). Magnification is 500×. FIG. 4C: Phylogenetic relationships among the mouse and human lipin protein family members. Multiple sequence alignment and phylogenetic tree were calculated using the ClustalX (Thompson et al. (1994) *Nucleic Acids Res.* 22: 4673–4680) and displayed by the Njplot (Perrieren and Gouy (1996) *Biochimie* 78: 364–369) programs. Tree topology is corroborated by 100% bootstrap support (1000 replicates) at all nodes. Homologous chromosomal locations of the corresponding orthologous gene pairs in the mouse (MMU) and human (HSA) genomes are indicated in parentheses. Lpin1 was initially mapped in the fld mutant strain (Rowe et al. (1996) *Mamm. Genome* 7: 555–557), and Lpin2 and Lpin3 were mapped in this study using a radiation hybrid panel (see Example 1). Genomic localization of the human LPIN genes was determined from database resources (reference 26 and the GenBank annotation for AL031667).

FIG. 5A through 5C illustrate that lipin deficiency attenuates obesity in a genetic model of obesity. FIG. 5A shows that daily food consumption is the same in ob and fld-ob mice. FIG. 5B shows that weight gain is reduced in fld-ob compared to ob mice. FIG. 5C illustrates an ob and an fld-ob mouse.

DETAILED DESCRIPTION

Figure 2A:
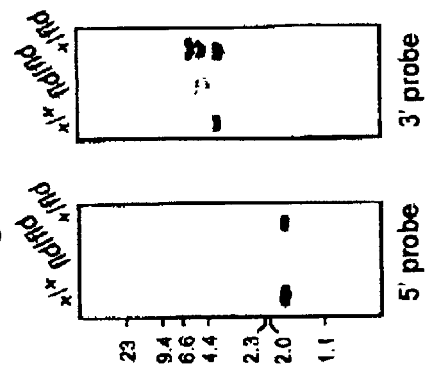
FIGS. 2A through 2D illustrate the structure of fld and $fld^{2J}$ mutant alleles.

This invention pertains to the identification and isolation of a gene implicated in the fatty liver dystrophy (fld) phenotype. An fld mutant mouse exhibits an array of abnormalities in lipid and glucose metabolism. During the neonatal period (1–10 days), fld mice have hypertriglyceridemia and a triglyceride filled, fatty liver. These features disappear by the age of 18–21 days. At this point, other abnormalities appear and persist throughout the animal's lifetime. Most notable is reduced weight gain and failure to accumulate normal amounts of adipose tissue. The fld mice also develop glucose intolerance and hyperinsulinemia, a whole body tremor, and have increased susceptibility to atherosclerosis; it is believed that these represent secondary manifestations of the impaired *adipose tissue development and metabolism.

It is believed that, prior to this invention the genes implicated in the fld phenotype were unknown. This invention relates to the isolation of both mouse and human forms of a novel gene, designated herein as Lpin1 and LPIN1 for mouse and human, respectively, that is rearranged in the fld genome leading to a null allele.

This gene and/or the mRNA, and/or the protein it encodes provide good targets for screening for agents that modulate adipocyte differentiation. Such agents are expected to be useful in the treatment of obesity, diabetes, and/or related pathologies. In addition, modulators are expected to be effective in regulating fat accumulation and hence weight gain or loss. It is also believed that one or more symptoms of lipodystrophy can be mitigated by increasing levels of an Lpin1 gene product in an organism.

Conversely it is believed that, at lest in certain cases (e.g. pathologies characterized by Overexpression of 1 pin) fat accumulation can be diminished by inhibiting expression or activity of lipin.

I. Assays for Agents that Modulate Lpin Expression.

As indicated above, in one aspect, this invention pertains to the discovery of genes (e.g. Lpin1) whose inactivation results in a lipodystrophic phenotype. The Lpin1 gene, or gene product(s) (e.g. mRNA, lipin protein, etc.) provide good targets for new agents that modulate adipocyte differentiation and/or modulate fat accumulation. Thus, in one embodiment, this invention provides methods of screening for agents that modulate Lpin1 expression and/or activity and hence adipocyte differentiation and/or fat accumulation. The methods preferably involve detecting a change in the expression level and/or activity level of a Lpin1 gene or gene product (e.g. Lpin protein) in cell(s) contacted with the test agent in question. An elevated Lpin1 expression level or activity level in the presence of the agent, e.g., as compared to a negative control where the test agent is absent or at reduced concentration indicates that the agent upregulates Lpin1 activity or expression. Conversely, decreased Lpin1 expression level or activity level in the presence of the agent as compared to a negative control where the test agent is absent or at reduced concentration indicates that the agent down-regulates Lpin1 activity or expression.

Expression levels of a gene can be altered by changes in the transcription of the gene product (i.e. transcription of mRNA), and/or by changes in translation of the gene product (i.e. translation of the protein), and/or by post-translational modification(s) (e.g. protein folding, glycosylation, etc.). Thus preferred assays of this invention include assaying for level of transcribed mRNA (or other nucleic acids derived from the Lpin1 gene), level of translated protein, activity of translated protein, etc. Examples of such approaches are described below.

A) Nucleic-Acid Based Assays.

1) Target Molecules.

Changes in expression level can be detected by measuring changes in mRNA and/or a nucleic acid derived from the mRNA (e.g. reverse-transcribed cDNA, etc.). In order to measure the Lpin1 expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I Theory and Nucleic Acid Preparation,* Elsevier, N.Y. and Tijssen ed.

In a preferred embodiment, the "total" nucleic acid is isolated from a given sample using, for example, an acid guanidinium-phenol-chloroform extraction method and polyA+mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology,* F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g, Innis, et al., (1990) *PCR Protocols. A guide to Methods and Application.* Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) of Lpin1 in a sample, the nucleic acid sample is one in which the concentration of the Lpin1 mRNA transcript(s), or the concentration of the nucleic acids derived from the Lpin1 mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the Lpin1-containing nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-Based Assays.

Using the Lpin1 sequences provided herein (see, e.g., SEQ ID Nos: 1 and 2) detecting and/or quantifying the Lpin1 transcript(s) can be routinely accomplished using nucleic acid hybridization techniques (see, e.g., Sambrook et al. supra). For example, one method for evaluating the presence, absence, or quantity of Lpin1 reverse-transcribed cDNA involves a "Southern Blot". In a Southern Blot, the DNA (e.g., reverse-transcribed Lpin1 mRNA), typically fragmented and separated on an electrophoretic gel, is hybridized to a probe specific for Lpin1 (or to a mutant thereof). Comparison of the intensity of the hybridization signal from the Lpin11 probe with a "control" probe (e.g. a probe for a "housekeeping gene) provides an estimate of the relative expression level of the target nucleic acid.

Alternatively, the Lpin1 mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target Lpin1 mRNA. Appropriate controls (e.g. probes to housekeeping genes) provide a reference for evaluating relative expression level.

An alternative means for determining the Lpin1 expression level is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-Based Assays.

In another embodiment, amplification-based assays can be used to measure Lpin1 expression (transcription) level. In such amplification-based assays, the target nucleic acid sequences (i.e., Lpin1) act as template(s) in amplification reaction(s) (e.g. Polymerase Chain Reaction (PCR) or reverse-transcription PCR (RT-PCR)). In a quantitative amplification, the amount of amplification product will be proportional to the amount of template (e.g., Lpin1 mRNA) in the original sample. Comparison to appropriate (e.g. healthy tissue or cells unexposed to the test agent) controls provides a measure of the Lpin1 transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al. (1990) Academic Press, Inc. N.Y. The known nucleic acid sequence(s) for Lpin1 are sufficient to enable one of skill to routinely select primers to amplify any portion of the gene.

4) Hybridization Formats and Optimization of Hybridization Conditions.

a) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high-density arrays is also described in U.S. Pat. Nos. 5,744,305, 5,800,992 and 5,445,934.

b) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach,* IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^{3}H$, $^{125}I$, $^{35}S$, $^{14}C$, or $^{32}P$-labelled probes or the like. Other labels include ligands that bind to labeled antibodies, fluorophores, chemiluminescent agents, enzymes, and antibodies that can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol.* 24: *Hybridization With Nucleic Acid Probes,* Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of Lpin1 expression levels can be full length or less than the full length of the Lpin1 or mutants thereof. Shorter probes are empirically tested for specificity. Preferred probes are sufficiently long so as to specifically hybridize with the Lpin1 target nucleic acid(s) under stringent conditions. The preferred size range is from about 20 bases to the length of the Lpin1 mRNA, more preferably from about 30 bases to the length of the Lpin1 mRNA, and most preferably from about 40 bases to the length of the Lpin1 mRNA.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label can be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol.* 24: *Hybridization With Nucleic Acid Probes,* P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science,* 281: 2013–2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016–2018).

B) Polypeptide-Based Assays.

1) Assay Formats.

In addition to, or in alternative to, the detection of Lpin1 nucleic acid expression level(s), alterations in expression of lipin can be detected and/or quantified by detecting and/or quantifying the amount and/or activity of translated lipin polypeptide.

2) Detection of Expressed Protein

The polypeptide(s) encoded by the Lpin1 gene can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the lipin polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol.* 182: *Guide to Protein Purification,* Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to a domain of the antibody.

In preferred embodiments, the lipin polypeptide(s) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume* 37: *Antibodies in Cell Biology,* Academic Press, Inc. New York; Stites & Terr (1991) *Basic and Clinical Immunology 7th Edition.*

Immunological binding assays (or immunoassays) typically utilize a "capture agent" to specifically bind to and often immobilize the analyte (lipin polypeptide). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom (1985) *J. Immunol.,* 135: 2589–2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (lipin polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The amount of target polypeptide bound to the antibody may be determined either by measuring the amount of target polypeptide present in an polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind lipin polypeptide(s), either alone or in combination. In the case where the antibody that binds lipin polypeptide is not labeled, a different detectable marker, for example, an enzyme-labeled antibody capable of binding to the monoclonal antibody which binds the lipin polypeptide, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds lipin polypeptides is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein are commercially available or can be produced as described below.

3) Antibodies to Lipin Polypeptides.

Either polyclonal or monoclonal antibodies may be used in the immunoassays of the invention described herein. Polyclonal antibodies are preferably raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptides encoded by Lpin1 or variants thereof.

If desired, the immunizing peptide may be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology,* Wiley Interscience).

Preferably, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')^{2'}$, and/or single-chain antibodies (e.g. scFv) which are capable of binding an epitopic determinant. Also, in this context, the term "mab's of the invention" refers to monoclonal antibodies with specificity for a polypeptide encoded by Lpin1.

The general method used for production of hybridomas secreting mAbs is well known (Kohler and Milstein (1975) *Nature,* 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature,* 348: 552–554; Hoogenboom et al. (1991) *Nucleic Acids Res.* 19: 4133–4137).

Since the antibody fragments on the surface of the phage are functional, phage bearing antigen binding antibody fragments can be separated from non-binding phage by antigen affinity chromatography (McCafferty et al. (1990) *Nature,* 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature,* 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581–597; Marks et al. (1993). *Bio/Technology.* 10: 779–783; Griffiths et al. (1993) *EMBO J.* 12: 725–734; Clackson et al. (1991) *Nature.* 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581–597; Griffiths et al. (1993) *EMBO J.* 12: 725–734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Assay Optimization.

The assays of this invention have immediate utility in screening for agents that modulate the Lpin1 expression and/or activity in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription the Lpin1 gene, nucleic acid based assays are preferred.

Routine selection and optimization of assay formats is well known to those of ordinary skill in the art.

D) Pre-Screening for Agents that Bind Lpin1 or Lipin Polypeptide

In certain embodiments it is desired to pre-screen test agents for the ability to interact with (e.g. specifically bind to) a Lpin1 (or mutant/allele) nucleic acid or polypeptide. Specifically, binding test agents are more likely to interact with and thereby modulate Lpin1 expression and/or activity. Thus, in some preferred embodiments, the test agent(s) are pre-screened for binding to Lpin1 nucleic acids or to lipin proteins before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the lipin protein or nucleic acid is immobilized and exposed to a test agent (which can be labeled), or alternatively, the lest agent(s) are immobilized and exposed to an lipin protein or to a Lpin1 nucleic acid (which can be labeled). The immobilized moiety is then washed to remove any unbound material and the bound test agent or bound Lpin1 nucleic acid or protein is detected (e.g. by detection of a label attached to the bound molecule). The amount of immobilized label is proportional to the degree of binding between the lipin protein or nucleic acid and the test agent.

E) Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control, preferably where the difference is statistically significant (e.g. at greater than 80%, preferably greater than about 90%, more preferably greater than about 98%, and most preferably greater than about 99% confidence level). Most preferred "positive" assays show at least a 1.2 fold, preferably at least a 1.5 fold, more preferably at least a 2 fold, and most preferably at least a 4 fold or even a 10-fold difference from the negative control.

F) Agents for Screening: Combinatorial Libraries (e.g., Small Organic Molecules).

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) *J. Med. Chem.*, 37(9): 1233–1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, 14 Oct. 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309–314), and PCT/US96/10287), carbohydrate libraries (see, e.g., Liang et al. (1996) *Science,* 274: 1520–1522, and U.S. Pat. No. 5,593,853), and small organic molecule libraries (see, e.g., benzodiazepines, Baum (1993) C&EN, Jan. 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. Nos. 5,506, 337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

G) High Throughput Screening

Any of the assays for compounds modulating the accumulation or degradation of metabolic products described herein are amenable to high throughput screening. Preferred assays detect increases or decreases in Lpin1 transcription and/or translation in response to the presence of a test compound.

The cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

H) Modulator Databases.

In certain embodiments, the agents that score positively in the assays described herein (e.g. show an ability to modulate Lpin1 expression) can be entered into a database of putative and/or actual modulators of Lpin1 expression. The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

II. Identification of Mutations in the LPIN1 Gene in Human Lipodystrophy, Obesity, Diabetes, and Atherosclerosis.

In another embodiment, this invention provides methods of detecting a mutation (e.g. insertion, deletion, point mutation, etc.) in a LPIN1 nucleic acid or in a polypeptide expressed from a LPIN1 nucleic acid. Identification of such mutations identifies/characterizes a lipodystrophic phenotype or a susceptibility to or likelihood of developing lipodystrophy, obesity, diabetes, atherosclerosis, and related pathologies. In other preferred embodiments, the methods involve detecting a LPIN1 gene product (e.g. mRNA, polypeptide, etc.) where an alteration in the amount or activity of LPIN1 gene product from the organism indicates that the organism has, or is susceptible to, a lipodystrophic phenotype, obesity, diabetes or atherosclerosis.

Expression levels of a LPIN1 gene product can be determined according to standard methods well known to those of skill in the art (see, e.g., description of methods provided above). Similarly, mutations in LPIN1 nucleic acids and/or lipin polypeptides can be identified according to standard methods. Thus, for example, mutations in nucleic acids can be readily identified using single-probe and/or array-based hybridization methods (see, e.g., Wang et al. (1998) *Science* 280: 1077–1082; Chee et al. (1996) 274: 610–614), various polymerase chain reaction (PCR) assays (e.g. that specifically amplify only the mutated variant), various ligase assays, nucleic acid sequencing, and the like. Mutations in polypeptides can easily be detected by changes in polypeptide mobility (e.g. electrophoretically), by mass spectroscopy, by the use of antibodies specific to the mutated polypeptide and the like.

III. Mitigation of Symptoms of Lipodystrophy, Obesity, Diabetes, Atherosclerosis and Related Pathologies.

In still another embodiment, this invention provides methods and compositions to mitigate symptoms of lipodystrophy, obesity, diabetes, atherosclerosis and related pathologies. The methods generally involve increasing or decreasing lipin protein concentration and/or activity in or near a cell, e.g., an adipocyte or an adipocyte precursor. This can be accomplished by transforming a cell (e.g. an adipocyte precursor cell) so that it expresses altered (e.g. elevated) levels of endogenous Lpin1/LPIN1 or so that it expresses lipin from an exogenous transfected Lpin1/LPIN1 nucleic acid, or by contacting the cell(s) with lipin protein(s) through local or systemic administration of a lipin protein, or agent which modulates the expression and/or activity of lipin.

As used herein, the term "adipocyte precursor cells" refers to any or all of those cells that have the capacity to ultimately form, or contribute to the formation of, new fat tissue. This includes various cells in different stages of differentiation. Adipocyte progenitor cells also include cells that have been isolated and manipulated in vitro, e.g., subjected to stimulation with agents such as hormones, cytokines, growth factors or even genetically engineered cells.

The term "adipocyte precursor cell" is also used to particularly refer to those cells that are located within, are in contact with, or migrate towards (i.e., "home to"), adipocyte progenitor tissue and which cells directly or indirectly stimulate the formation of fat tissue. As such, the progenitor cells may be cells that ultimately differentiate into mature adipocytes themselves, or cells that, upon stimulation, attract further progenitor cells or promote nearby cells to differentiate into adipocytes. Cells affecting adipocyte formation indirectly may do so by the elaboration of various growth factors or cytokines, or by their physical interaction with other cell types.

A) Transformation of Cells to Increase Lipin Production.

In a preferred embodiment, the Lpin1/LPIN1 nucleic acids (e.g., cDNA(s)) are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino and Gould-Fogerite (1988) *BioTechniques* 6(7): 682–691; Rose U.S. Pat. No. 5,279,833; WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808–813; Nabel and Felgner (1993) *TIBTECH* 11: 211–217; Mitani and Caskey (1993) *TIBTECH* 11: 162–166; Mulligan (1993) *Science,* 926–932; Dillon (1993) *TIBTECH* 11: 167–175; Miller (1992) *Nature* 357: 455–460; Van Brunt (1988) *Biotechnology* 6(10): 1149–1154; Vigne (1995) Restorative Neurology and Neuroscience 8: 35–36; Kremer and Perricaudet (1995) *British Medical Bulletin* 51(1) 31–44; Haddada et al. (1995) in *Current Topics in Microbiology and Immunology,* Doerfler and Böhm (eds) Springer-Verlag, Heidelberg Germany; and Yu et al., (1994) *Gene Therapy,* 1:13–26.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology,* Third Edition Paul (ed) Raven Press, Ltd., New York and the references therein, and Yu et al., Gene Therapy (1994) supra). The vectors are optionally pseudotyped to extend the host range of the vector to cells which are not infected by the retrovirus corresponding to the vector. The vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invest.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4: 2072–2081; Hermonat and Muzyczka (1984) Proc. Natl. Acad. Sci. USA, 81: 6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996. Other suitable viral vectors include herpes virus and vaccinia virus.

U.S. Pat. Nos. 5,942,496 and 5,763,416 disclose methods, compositions, kits and devices for use in transferring nucleic acids into bone cells in situ and/or for stimulating bone progenitor cells (see also, Evans and Robbins (1995) *J. Bone and Joint Surgery,* 77-A(7):1103–1114, Wolff et al. (1992) *J. Cell Sci.,* 103:1249–1259).

B) Administration of Exogenously Produced Lipin or Inhibitors or Lipin Expression or Activity.

The lipin proteins (or biologically active fragments thereof) of this invention are or inhibitors of lipin expression and/or activity are useful for intravenous, parenteral, topical, oral, or local administration (e.g., by aerosol or transdermally). Particularly preferred modes of administration include intra-arterial injection, injection into fracture sites or delivery in a biodegradable matrix. The lipin proteins are typically combined with a pharmaceutically acceptable carrier (excipient) to form a pharmacological composition. Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the rout of administration of the anti-mitotic agent and on the particular physio-chemical characteristics the agent.

The pharmaceutical compositions can be administered in a variety of unit dosage forms depending upon the method of administration. For example, unit dosage forms suitable for oral administration include powder, tablets, pills, capsules and lozenges. It is recognized that the lipin protein(s), if administered orally, are preferably protected from digestion. This is typically accomplished either by complexing the protein with a composition to render it resistant to acidic and enzymatic hydrolysis or by packaging the protein in an appropriately resistant carrier such as a liposome. Means of protecting compounds from digestion are well known in the art (see, e.g., U.S. Pat. No. 5,391,377 describing lipid compositions for oral delivery of therapeutic agents).

The pharmaceutical compositions of this invention are particularly useful for topical administration e.g., in surgical wounds to treat facilitate bone reconstruction and/or repair. In another embodiment, the compositions are useful for parenteral administration, such as intravenous administration or administration into a body cavity or lumen of an organ. The compositions for administration will commonly comprise a solution of the lipin protein dissolved in a pharmaceutically acceptable carrier, preferably an aqueous carrier for water-soluble proteins. A variety of carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of lipin protein in these formulations can vary widely, and will be selected primarily based on fluid volumes, viscosities, body weight and the like in accordance with the particular mode of administration selected and the patient's needs. Typically the lipin proteins are utilized in the form of a pharmaceutically acceptable solution (including reconstitution from a lyophilized form). It is optimal to solubilize the protein at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml may be desirable.

As alluded to above, the dosage regimen will be determined by the clinical indication being addressed, as well as by various patient variables (e.g. weight, age, sex) and clinical presentation (e.g. extent of injury, site of injury, etc.). In general, the dosage of lipin protein will be in the range of from 1 to about 10000 $\mu$g, preferably from about about 10 to 1000 $\mu$g, more preferably from about 10 to 100 $\mu$g.

C) Inhibition of Fat Accumulation.

It is demonstrated herein that lipin deficiency in fld mice is associated with a major reduction in total body fat. In certain embodiments, this invention contemplates the reduction of body fat by inhibiting endogenous lipin expression or activity. Such methods are particularly contemplated in pathologies (e.g. obesity), particularly where lipin is overexpressed.

Lipin expression can upregulated or inhibited using a wide variety of approaches known to those of skill in the art. For example, methods of inhibiting lipin expression include, but are not limited to antisense molecules, lipin specific ribozymes, lipin specific catalytic DNAs, intrabodies directed against lipin proteins, RNAi, gene therapy approaches that knock out lipins, and small organic molecules that inhibit lipin expression/overexpression or that block receptor activity that is required to induce lipin expression. It will be appreciated that the methods used to alter lipin expression/activity can generally also be used to alter expression/activity of lipin homologues.

1) Antisense Approaches.

Llipin gene expression can be downregulated or entirely inhibited by the use of antisense molecules. An "antisense sequence or antisense nucleic acid" is a nucleic acid that is complementary to the coding lipin mRNA nucleic acid sequence or a subsequence thereof. Binding of the antisense molecule to the lipin mRNA interferes with normal translation of the lipin polypeptide.

Thus, in accordance with preferred embodiments of this invention, preferred antisense molecules include oligonucleotides and oligonucleotide analogs that are hybridizable with lipin messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of lipin polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species that are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

In one particularly preferred embodiment, the internucleotide phosphodiester linkage is replaced with a peptide linkage. Such peptide nucleic acids tend to show improved stability, penetrate the cell more easily, and show enhances affinity for their target. Methods of making peptide nucleic acids are known to those of skill in the art (see, e.g., U.S. Pat. Nos. 6,015,887, 6,015,710, 5,986,053, 5,977,296, 5,902,786, 5,864,010, 5,786,461, 5,773,571, 5,766,855, 5,736,336, 5,719,262, and 5,714,331).

Oligonucleotides may also include species that contain at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of lipin to inhibit the function of that RNA.

The oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. It is also will known to prepare other oligonucleotide such as phosphorothioates and alkylated derivatives.

Using the known sequence of the lipin gene(s)/cDNA(s) identified herein, appropriate and effective antisense oligonucleotide sequences can be readily determined.

2) Catalytic RNAs and DNAs a) Ribozymes.

In another approach, lipin expression can be inhibited by the use of ribozymes. As used herein, "ribozymes" include RNA molecules that contain anti-sense sequences for specific recognition, and an RNA-cleaving enzymatic activity. The catalytic strand cleaves a specific site in a target (lipin) RNA, preferably at greater than stoichiometric concentration. Two "types" of ribozymes are particularly useful in this invention, the hammerhead ribozyme (Rossi et al. (1991) *Pharmac. Ther.* 50: 245–254) and the hairpin ribozyme (Hampel et al. (1990) *Nucl. Acids Res.* 18: 299–304, and U.S. Pat. No. 5,254,678).

Because both hammerhead and hairpin ribozymes are catalytic molecules having antisense and endoribonucleotidase activity, ribozyme technology has emerged as a powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Accordingly, within one aspect of the present invention ribozymes are provided which have the ability to inhibit lipin expression. Such ribozymes can be in the form of a "hammerhead" (for example, as described by Forster and Symons (1987) *Cell* 48: 211–220,; Haseloff and Gerlach (1988) *Nature* 328: 596–600; Walbot and Bruening (1988) *Nature* 334: 196; Haseloff and Gerlach (1988) *Nature* 334: 585) or a "hairpin" (see, e.g. U.S. Pat. No. 5,254,678 and Hampel et al., European Patent Publication No. 0 360 257, published Mar. 26, 1990), and have the ability to specifically target, cleave and lipin nucleic acids.

The sequence requirement for the hairpin ribozyme is any RNA sequence consisting of nnnbn*gucnnnnnn (where N*G is the cleavage site, where B is any of G, C, or U, and where N is any of G, U, C, or A) (SEQ ID NO:12). Suitable lipin of recognition or target sequences for hairpin ribozymes can be readily determined from the lipin sequence(s) identified herein.

The preferred sequence at the cleavage site for the hammerhead ribozyme is any RNA sequence consisting of NUX (where N is any of G, U, C, or A and X represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al. (1990) *Biochemistry* 29: 10695–10702).

Cech et al. (U.S. Pat. No. 4,987,071,) has disclosed the preparation and use of certain synthetic ribozymes which have endoribonuclease activity. These ribozymes are based on the properties of the Tetrahymena ribosomal RNA self-splicing reaction and require an eight base pair target site. A temperature optimum of 50° C. is reported for the endoribonuclease activity. The fragments that arise from cleavage contain 5' phosphate and 3' hydroxyl groups and a free guanosine nucleotide added to the 5' end of the cleaved RNA. The preferred ribozymes of this invention hybridize efficiently to target sequences at physiological temperatures, making them particularly well suited for use in vivo.

The ribozymes of this invention, as well as DNA encoding such ribozymes and other suitable nucleic acid molecules can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette (see, e.g., Cotten and Birnstiel (1989) *EMBO J* 8(12):3861–3866; Hempel et al. (1989) *Biochem.* 28: 4929–4933, etc.).

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The ribozyme molecule also can be in a host prokaryotic or eukaryotic cell in culture or in the cells of an organism/patient. Appropriate prokaryotic and eukaryotic cells can be transfected with an appropriate transfer vector containing the DNA molecule encoding a ribozyme of this invention. Alternatively, the ribozyme molecule, including nucleic acid molecules encoding the ribozyme, may be introduced into the host cell using traditional methods such as transformation using calcium phosphate precipitation (Dubensky et al. (1984) *Proc. Natl. Acad. Sci., USA,* 81: 7529–7533), direct microinjection of such nucleic acid molecules into intact target cells (Acsadi et al. (1991) *Nature* 352: 815–818), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al. (1990) *Proc. Natl. Acad. Sci., USA,* 89 :6094), lipofection (Felgner et al. (1989) *Proc. Natl. Acad. Sci. USA* 84: 7413–7417), microprojectile bombardment (Williams et al. (1991) *Proc. Natl. Acad. Sci., USA,* 88: 2726–2730), polycation compounds such as polylysine, receptor specific ligands, liposomes entrapping the nucleic acid molecules, spheroplast fusion whereby *E coli* containing the nucleic acid molecules are stripped of their outer cell walls and fused to animal cells using polyethylene glycol, viral transduction, (Cline et al., (1985) *Pharmac. Ther.* 29: 69; and Friedmann et al. (1989) *Science* 244: 1275), and DNA ligand (Wu et al (1989) *J. Biol. Chem.* 264: 16985–16987), as well as psoralen inactivated viruses such as Sendai or Adenovirus. In one preferred embodiment, the ribozyme is introduced into the host cell utilizing a lipid, a liposome or a retroviral vector.

When the DNA molecule is operatively linked to a promoter for RNA transcription, the RNA can be produced in the host cell when the host cell is grown under suitable conditions favoring transcription of the DNA molecule. The vector can be, but is not limited to, a plasmid, a virus, a retrotransposon or a cosmid. Examples of such vectors are disclosed in U.S. Pat. No. 5,166,320. Other representative vectors include, but are not limited to adenoviral vectors (e.g., WO 94/26914, WO 93/9191; Kolls et al. (1994) PNAS 91(1):215–219; Kass-Eisler et al., (1993) *Proc. Natl. Acad. Sci., USA,* 90(24): 11498–502, Guzman et al. (1993) *Circulation* 88(6): 2838–48, 1993; Guzman et al. (1993) *Cir. Res.* 73(6):1202–1207, 1993; Zabner et al. (1993) *Cell* 75(2): 207–216; Li et al. (1993) *Hum Gene Ther.* 4(4): 403–409; Caillaud et al. (1993) *Eur. J Neurosci.* 5(10): 1287–1291), adeno-associated vector type 1 ("AAV-1") or adeno-associated vector type 2 ("AAV-2") (see WO 95/13365; Flotte et al. (1993) *Proc. Natl. Acad. Sci., USA,* 90(22) :10613–10617), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick and Burck (1991) *Gene Therapy: Application of Molecular Biology,* Elsevier Science Publishing Co., Inc., New York, N.Y., and Kreigler (1990) *Gene Transfer and Expression: A Laboratory Manual,* W. H. Freeman and Company, New York.

To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo. Suitable transfector vectors for in vivo expression are discussed below.

b) Catalytic DNA

In a manner analogous to ribozymes, DNAs are also capable of demonstrating catalytic (e.g. nuclease) activity. While no such naturally-occurring DNAs are known, highly catalytic species have been developed by directed evolution and selection. Beginning with a population of $10^{14}$ DNAs containing 50 random nucleotides, successive rounds of selective amplification, enriched for individuals that best promote the $Pb^{2+}$-dependent cleavage of a target ribonucleoside 3'-O-P bond embedded within an otherwise all-DNA sequence. By the fifth round, the population as a whole carried out this reaction at a rate of 0.2 $min^{-1}$. Based on the sequence of 20 individuals isolated from this population, a simplified version of the catalytic domain that operates in an intermolecular context with a turnover rate of 1 $min^{-1}$ (see, e.g., Breaker and Joyce (1994) *Chem Biol* 4: 223–229.

In later work, using a similar strategy, a DNA enzyme was made that could cleave almost any targeted RNA substrate under simulated physiological conditions. The enzyme is comprised of a catalytic domain of 15 deoxynucleotides, flanked by two substrate-recognition domains of seven to eight deoxynucleotides each. The RNA substrate is bound through Watson-Crick base pairing and is cleaved at a particular phosphodiester located between an unpaired purine and a paired pyrimidine residue. Despite its small size, the DNA enzyme has a catalytic efficiency (kcat/Km) of approximately $10^9$ $M^{-1}min^{-1}$ under multiple turnover conditions, exceeding that of any other known nucleic acid enzyme. By changing the sequence of the substrate-recognition domains, the DNA enzyme can be made to target different RNA substrates (Santoro and Joyce (1997) *Proc. Natl. Acad. Sci., USA,* 94(9): 4262–4266). Modifying the appropriate targeting sequences (e.g. as described by Santoro and Joyce, supra.) the DNA enzyme can easily be retargeted to lipin mRNA thereby acting like a ribozyme.

3) Knocking Out Lipin

In another approach, lipin can be inhibited/downregulated simply by "knocking out" the gene.

In certain embodiments, this invention provides animals in which the lipin gene is knocked out". Such animals can be heterozygous or homozygous for the knockout.

Typically this is accomplished by disrupting the lipin gene(s), the promoter regulating the lipin gene(s) or sequences between the endogenous promoter(s) and the gene(s). Such disruption can be specifically directed to lipin nucleic acids (e.g. lipin1, and/or lipin2, and/or lipin3) by homologous recombination where a "knockout construct" contains flanking sequences complementary to the domain to which the construct is targeted. Insertion of the knockout construct (e.g. into a lipin gene) results in disruption of that gene.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, the cell and its progeny will no longer express the gene or will express it at a decreased level, as the DNA is now disrupted by the antibiotic resistance gene.

Knockout constructs can be produced by standard methods known to those of skill in the art. The knockout construct can be chemically synthesized or assembled, e.g., using recombinant DNA methods. The DNA sequence to be used in producing the knockout construct is digested with a particular restriction enzyme selected to cut at a location(s) such that a new DNA sequence encoding a marker gene can be inserted in the proper position within this DNA sequence. The proper position for marker gene insertion is that which will serve to prevent expression of the native lipin gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the gene to be suppressed so as to keep the length of the knockout construct comparable to the original genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, however typically it is an antibiotic resistance gene or other gene whose expression or presence in the genome can easily be detected. The marker gene is usually operably linked to its own promoter or to another strong promoter from any source that will be active or can easily be activated in the cell into which it is inserted; however, the marker gene need not have its own promoter attached as it may be transcribed using the promoter of the gene to be suppressed. In addition, the marker gene will normally have a polyA sequence attached to the 3' end of the gene; this sequence serves to terminate transcription of the gene. Preferred marker genes are any antibiotic resistance gene including, but not limited to neo (the neomycin resistance gene) and beta-gal (beta-galactosidase).

After the genomic DNA sequence has been digested with the appropriate restriction enzymes, the marker gene sequence is ligated into the genomic DNA sequence using methods well known to the skilled artisan (see, e.g., Berger and Kimmel, *Guide to Molecular Cloning Techniques, Methods in Enzymology* volume 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, N.Y.; and *Current Protocols in Molecular Biology,* F. M. Ausubel et al., eds., Current Protocols, a joint venture between Greene Publishing Associates, Inc. and John Wiley & Sons, Inc., (1994) Supplement). The ends of the DNA fragments to be ligated are rendered compatible, e.g., by either cutting the fragments with enzymes that generate compatible ends, or by blunting the ends prior to ligation. Blunting is done using methods well known in the art, such as for example by the use of Klenow fragment (DNA polymerase I) to fill in sticky ends.

The production of knockout constructs and their use to produce knockout mice is well known to those of skill in the art (see, e.g., Dorfman et al. (1996) *Oncogene* 13: 925–931). The knockout constructs can be delivered to cells in vivo using gene therapy delivery vehicles (e.g. retroviruses, liposomes, lipids, dendrimers, etc.) as described above. Methods of knocking out genes are well described in the literature and essentially routine to those of skill in the art (see, e.g., Thomas et al. (1986) *Cell* 44(3): 419–428; Thomas, et al. (1987) *Cell* 51(3): 503–512)1; Jasin and Berg (1988) *Genes & Development* 2: 1353–1363; Mansour, et al. (1988) *Nature* 336: 348–352; Brinster, et al. (1989) *Proc Natl Acad Sci* 86: 7087–7091; Capecchi (1989) *Trends in Genetics* 5(3): 70–76; Frohman and Martin (1989) *Cell* 56: 145–147; Hasty, et al. (1991) *Mol Cell Bio* 11(11): 5586–5591; Jeannotte, et al. (1991) *Mol Cell Biol.* 11(11): 557814 5585; and Mortensen, et al. (1992) *Mol Cell Biol.* 12(5): 2391–2395.

The use of homologous recombination to alter expression of endogenous genes is also described in detail in U.S. Pat. No. 5,272,071, WO 91/09955, WO 93/09222, WO 96/29411, WO 95/31560, and WO 91/12650.

Production of the knockout animals of this invention is not dependent on the availability of ES cells. In various embodiments, knockout animals of this invention can be produced using methods of somatic cell nuclear transfer. In preferred embodiments using such an approach, a somatic cell is obtained from the species in which the lipin gene is to be knocked out. The cell is transfected with a construct that introduces a disruption in the lipin gene (e.g. via heterologous recombination) as described herein. Cells harboring a knocked out lipin gene are selected as described herein. The nucleus of such cells harboring the knockout is then placed in an unfertilized enucleated egg (e.g., eggs from which the natural nuclei have been removed by microsurgery). Once the transfer is complete, the recipient eggs contained a complete set of genes, just as they would if they had been fertilized by sperm. The eggs are then cultured for a period before being implanted into a host mammal (of the same species that provided the egg) where they are carried to term, culminating in the berth of a transgenic animal comprising a nucleic acid construct containing one or more disrupted lipin genes.

The production of viable cloned mammals following nuclear transfer of cultured somatic cells has been reported for a wide variety of species including, but not limited to frogs (McKinnell (1962) *J. Hered.* 53, 199–207), calves (Kato et al. (1998) *Science* 262: 2095–2098), sheep (Campbell et al. (1996) *Nature* 380: 64–66), mice (Wakayamaand Yanagimachi (1999) *Nat. Genet.* 22: 127–128), goats (Baguisi et al. (1999) *Nat. Biotechnol.* 17: 456–461), monkeys (Meng et al. (1997) *Biol. Reprod.* 57: 454–459), and pigs (Bishop et al. (2000) *Nature Biotechnology* 18: 1055–1059). Nuclear transfer methods have also been used to produce clones of transgenic animals. Thus, for example, the production of transgenic goats carrying the human antithrobin III gene by somatic cell nuclear transfer has been reported (Baguisi et al. (1999) *Nature Biotechnology* 17: 456–461).

Using methods of nuclear transfer as described in these and other references, cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass (CICM) cells. The cloned embryos can also be combined with fertilized embryos to produce chimeric embryos, fetuses and/or offspring.

Somatic cell nuclear transfer also allows simplification of transgenic procedures by working with a differentiated cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques.

Nuclear transfer techniques or nuclear transplantation techniques are known in the literature. See, in particular, Campbell et al. (1995) *Theriogenology,* 43:181; Collas et al. (1994) *Mol. Report Dev.,* 38:264–267; Keefer et al. (1994) *Biol. Reprod.,* 50:935–939; Sims et al. (1993) *Proc. Natl. Acad. Sci., USA,* 90:6143–6147; WO 94/26884; WO 94/24274, WO 90/03432, U.S. Pat. Nos. 5,945,577, 4,944, 384, 5,057,420 and the like.

4) Intrabodies.

In still another embodiment, lipin expression/activity is inhibited by transfecting the subject cell(s) (e.g., cells of the vascular endothelium) with a nucleic acid construct that expresses an intrabody. An intrabody is an intracellular antibody, in this case, capable of recognizing and binding to a lipin polypeptide. The intrabody is expressed by an "antibody cassette", containing a sufficient number of nucleotides coding for the portion of an antibody capable of binding to the target (lipin polypeptide) operably linked to a promoter that will permit expression of the antibody in the cell(s) of interest. The construct encoding the intrabody is delivered to the cell where the antibody is expressed intracellularly and binds to the target lipin, thereby disrupting the target from its normal action. This antibody is sometimes referred to as an "intrabody".

In one preferred embodiment, the "intrabody gene" (antibody) of the antibody cassette would utilize a cDNA, encoding heavy chain variable ($V_H$) and light chain variable ($V_L$) domains of an antibody which can be connected at the DNA level by an appropriate oligonucleotide as a bridge of the two variable domains, which on translation, form a single peptide (referred to as a single chain variable fragment, "sFv") capable of binding to a target such as an lipin protein. The intrabody gene preferably does not encode an operable secretory sequence and thus the expressed antibody remains within the cell.

Anti-lipin antibodies suitable for use/expression as intrabodies in the methods of this invention can be readily produced by a variety of methods. Such methods include, but are not limited to, traditional methods of raising "whole" polyclonal antibodies, which can be modified to form single chain antibodies, or screening of, e.g. phage display libraries to select for antibodies showing high specificity and/or avidity for lipin. Such screening methods are described above in some detail.

The antibody cassette is delivered to the cell by any of the known means. This discloses the use of a fusion protein comprising a target moiety and a binding moiety. The target moiety brings the vector to the cell, while the binding moiety carries the antibody cassette. Other methods include, for example, Miller (1992) *Nature* 357: 455–460; Anderson (1992) *Science* 256: 808–813; Wu, et al. (1988) *J. Biol. Chem.* 263: 14621–14624. For example, a cassette containing these (anti-lipin) antibody genes, such as the sFv gene, can be targeted to a particular cell by a number of techniques including, but not limited to the use of tissue-specific promoters, the use of tissue specific vectors, and the like. Methods of making and using intrabodies are described in detail in U.S. Pat. No. 6,004,940.

5) Small Organic Molecules.

In still another embodiment, lipin expression and/or lipin protein activity can be inhibited by the use of small organic molecules. Such molecules include, but are not limited to molecules that specifically bind to the DNA comprising the lipin promoter and/or coding region, molecules that bind to and complex with lipin mRNA, molecules that inhibit the signaling pathway that results in lipin upregulation, and molecules that bind to and/or compete with lipin polypeptides. Small organic molecules effective at inhibiting lipin expression can be identified with routine screening using the methods described herein.

The methods of inhibiting lipin expression described above are meant to be illustrative and not limiting. In view of the teachings provided herein, other methods of inhibiting lipin will be known to those of skill in the art.

V. Kits.

In still another embodiment, this invention provides kits for practice of the assays or use of the compositions described herein. In one preferred embodiment, the kits comprise one or more containers containing antibodies and/or nucleic acid probes and/or substrates suitable for detection of Lpin1 expression and/or activity levels. The kits may optionally include any reagents and/or apparatus to facilitate practice of the assays described herein. Such reagents include, but are not limited to buffers, labels, labeled or unlabeled antibodies, labeled nucleic acids, filter sets for visualization of fluorescent labels, blotting membranes, and the like.

In another embodiment, the kits can comprise a container containing an lipin protein, or a vector encoding a lipin protein and/or a cell comprising a vector encoding a lipin protein.

In addition, the kits may include instructional materials containing directions (i.e., protocols) for the practice of the assay methods of this invention or the administration of the compositions described here along with counterindications. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Lipodystrophy in the fld Mouse Results from Mutation in a Novel Nuclear Protein Mice carrying mutations in the fatty liver dystrophy (fld) gene exhibit features of human lipodystrophy, a genetically heterogeneous group of disorders characterized by loss of body fat, fatty liver, hypertriglyceridemia, insulin resistance, and increased suseptibility to atherosclerosis (Seip and Trygstad (1996) *Acta Paediatr. Scand. Suppl.* 413: 2–28; Senior and Gellis (1964) *Pediatrics* 33: 593–612; Dörfler et al. (1993) *Clin. Investig.* 71: 264–269; Garg (2000) *J. Clin. Endocrinol. Metab.* 85: 1776–1782). Through positional cloning, we have isolated the responsible gene, and characterized two independent mutant alleles, fld and $fld^{2J}$. The gene encodes a novel nuclear protein which we have named lipin (gene symbol Lpin1). Consistent with the observed reduction of adipose tissue mass in fld and $fld^{2J}$ mice, wild-type lipin mRNA is expressed at high levels in adipose tissue and is induced during differentiation of 3T3-L1 preadipocytes. Our results indicate that lipin is required for normal adipose tissue development, and provide a candidate gene for human lipodystrophy. Lipin defines a novel family of nuclear proteins containing at least three members in mammalian species, and homologs in distantly related organisms from man to yeast.

The initial description of the BALB/cByJ-fld mutant mouse (hereafter known as fld) focused on two features for which the mutation was named—presence of a triglyceride-filled fatty liver and a progressive neuropathy affecting peripheral nerve (Langner et al. (1989) *J. Biol. Chem.* 264: 7994–8003; Langner et al. (1991) *J. Biol. Chem.* 266: 11955–11964; Rehnmark et al. (1998) *J. Lipid Res.* 39: 2209–2217; Klingenspor et al. (1999) *J. Biol. Chem.* 274: 23078–23084). Subsequently, an independent mutant strain, C3H/HeJ-fld$^{2J}$ (known as fld$^{2J}$), with the same phenotype and a mutation allelic to fld was isolated (Mouse Genome Informatics Project: The Jackson Laboratory: Bar Harbor: Me. www.informatics.jax.org) (1999)). Our further characterization indicates that in addition to fatty liver and neuropathy, both fld and fld$^{2J}$ mutants exhibit markedly diminished adipose tissue depots with 50–90% reductions in white and brown fat pad mass (FIG. 1*a* and data not shown). Adipocytes in the affected tissue appear immature, with sparse lipid droplets (compare FIG. 1*b* and *c*). Similar reductions in adipose tissue mass and cellular lipid content have been observed in transgenic mice expressing a dominant negative transcription factor that interferes with adipocyte differentiation (Shimomura et al. (1998) Genes. Dev. 12: 3182–3194). In these mice, it has be n shown that reduction in leptin levels that results from diminished adipose tissue mass is responsible for the development of fatty liver, hypertriglyceridemia and insulin resistance (Shimomura et al. (1999) *Science* 401: 73–76). Analogously, fld mice exhibit significantly reduced plasma leptin levels (FIG. 1*d*) and insulin resistance, suggesting that the primary defect in fld and fld$^{2J}$ mice is impaired adipose tissue development, with other phenotypic features (i.e., fatty liver, hypertriglyceridemia, insulin resistance) occurring as secondary manifestations of the mutation.

To isolate the gene responsible for the fld phenotype we employed a positional cloning strategy. We previously identified three genes in the fld critical region (Peterfy et al. (1999) *Genomics* 62: 436–444), and now report that one of these, Lpin1 (formerly Kiaa0188), is mutated in both the fld and fld$^{2J}$ strains.

Figure 2B:
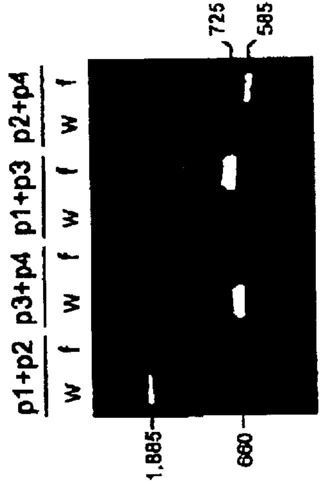
Figure 2C:
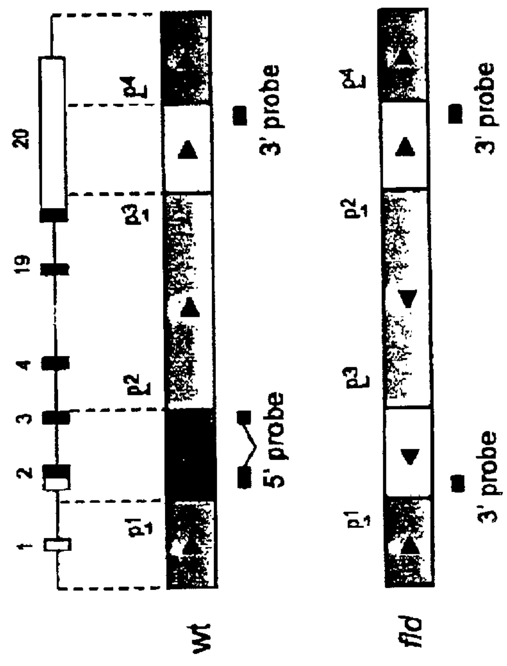

Characterization of Lpin1 revealed a complex rearrangement in the genome of fld mice compared to their wild-type littermates. Southern blot analysis using exonic DNA probes from the 5' and 3' ends of the gene indicated the presence of a deletion and duplication, respectively (FIG. 2*a*). PCR scanning of the gene uncovered additional alterations in fld DNA, with primer sets flanking the deleted and duplicated regions failing to amplify fld DNA (FIG. 2*b*). However, when forward or reverse primers from opposite ends of the gene were paired, PCR products were generated from fld DNA, indicating an internal inversion. Based on the integration of these results and additional Southern blot, PCR amplification and DNA sequence data (not shown), we determined that the fld mutant allele contains three gross abnormalities, depicted schematically in FIG. 2*c*: (i) the deletion of ~2 kb resulting in the elimination of exons 2 and 3, including the translation initiation site; (ii) the inversion of a large genomic region covering more than 40 kb and containing the majority of the coding sequence; and (iii) duplication of a 0.5-kb segment of the 3' UTR, with one copy at the position it occurs in the wild-type allele and a second copy carried along with the inverted region. The 5' and 3' ends of the fld allele remain intact (FIG. 2*c* and data not shown), indicating that the mutation is confined to Lpin1. The molecular mechanisms leading to the fld allele are unknown, although, the coincidence of chromosomal breakpoints at the deletion/inversion and inversion/duplication junctions suggests a concerted event rather than a series of independent steps (Okano et al. (1991) *J. Neurochem.* 56: 560–567). Furthermore, since no homologous sequences could be identified at the breakpoint regions, a mechanism involving non-homologous recombination is suggested.

Figure 2D:
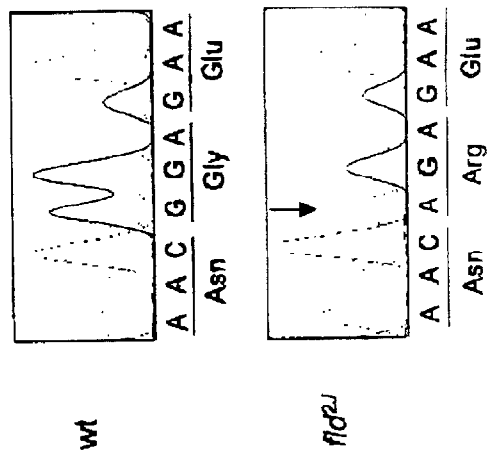
Figure 4D:
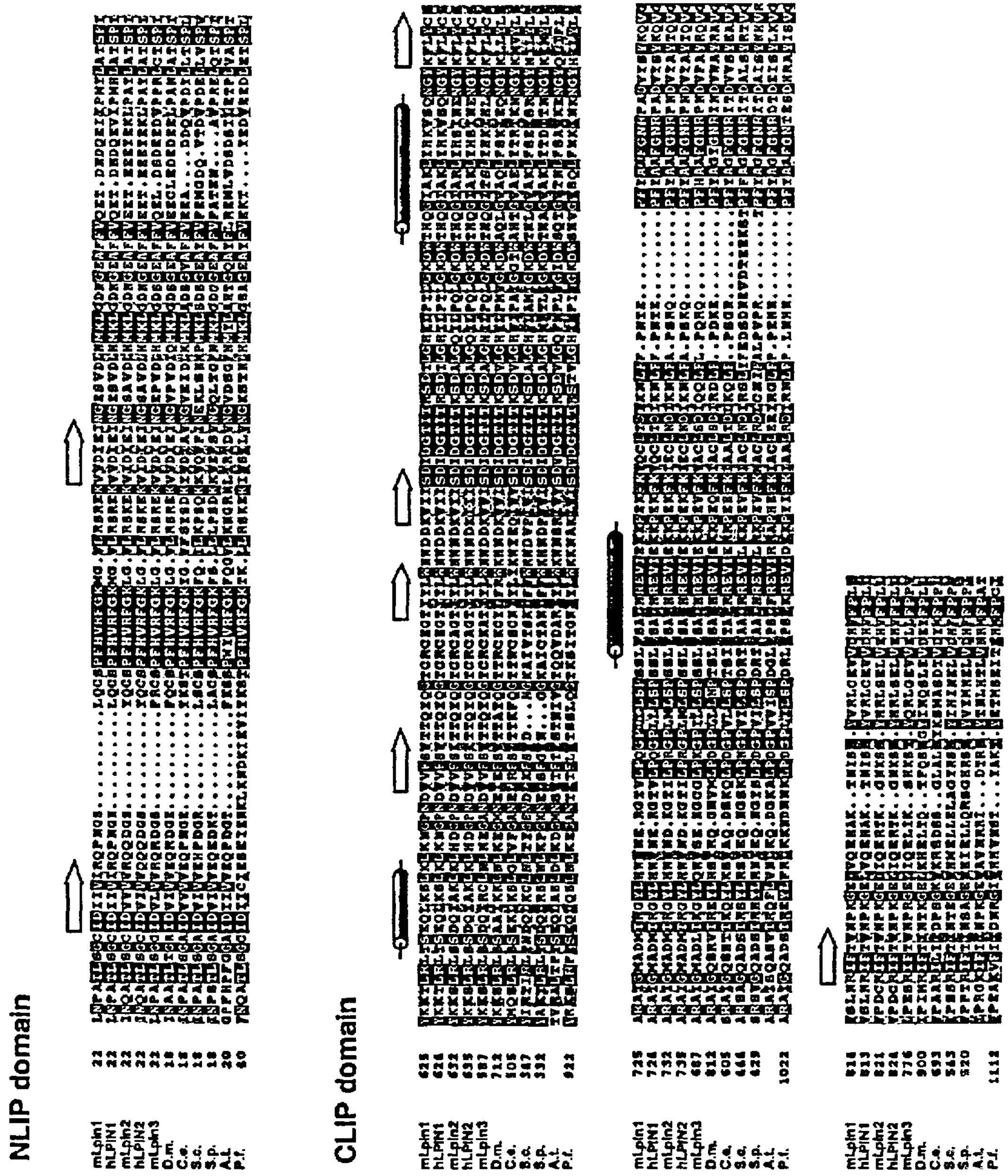
FIG. 4D: Alignments of the NLIP and CLIP domains showing positions of residues that are identical (black background) or similar (gray background) in at least 90% of the sequences. The asterisk above the NLIP sequence denotes the position of the Gly84Arg mutation in $fld^{2J}$ mice.
Figure 6:
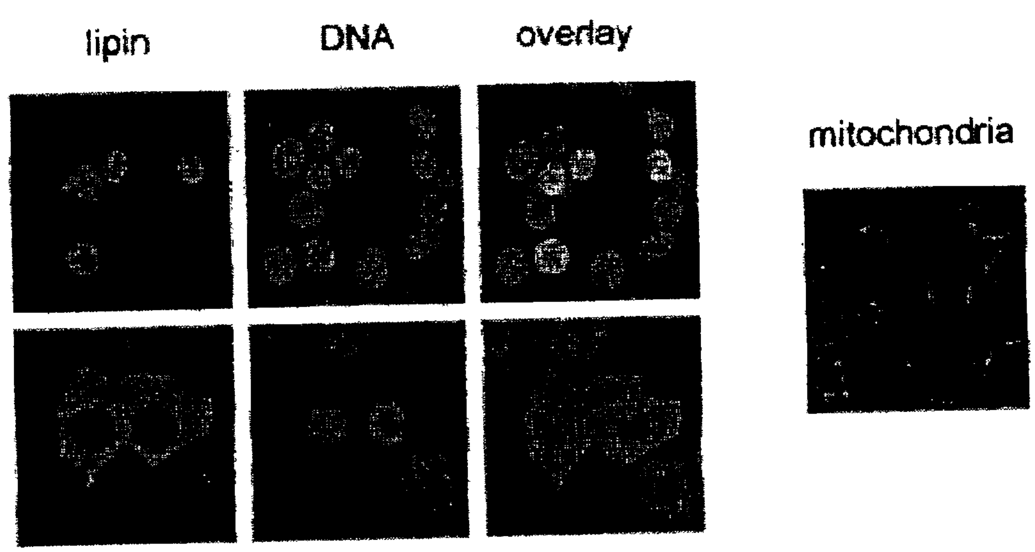
FIG. 6 illustrates the cellular localization of lipin.

In contrast to fld, PCR scanning of genomic DNA from the fld$^{2J}$ strain revealed no gross abnormalities in Lpin1 (not shown). We therefore sequenced lipin cDNA and genomic DNA prepared from tissues of fld$^{2J}$ and wild-type littermates, and detected a single point mutation resulting in a Gly84Arg substitution (FIG. 2*d*). As shown in FIG. 4*d*, Gly84 is invariably conserved in homologous sequences from diverse organisms including human, *Drosophila melanogaster, Caenorhabditis elegans, Arabidopsis thaliana, Saccharomyces cerevisiae, Schizosaccharomyces pombe* and *Plasmodium falciparum*. These data strongly suggest that the nonconservative mutation in the fld$^{2J}$ allele has a functional consequence on lipin activity.

Northern blot analysis of total RNA from wild-type mouse tissues revealed that lipin mRNA is prominently expressed in adipose tissue, skeletal muscle and testis (FIG. 3*a*). Lower level expression was also detected in kidney, lung, brain, and liver (the latter was detectable only with poly A+RNA). In addition to the ~5-kb transcript observed in these tissues, testis also exhibited an abundant ~3-kb transcript. Aberrant lipin mRNA levels were evident in tissue from mice homozygous for the fld and fld$^{2J}$ mutations. No mRNA was detectable in fld adipose tissue, whereas elevated mRNA levels were detected in fld$^{2J}$ adipose (FIG. 3*b*). Increased expression in fld$^{2J}$ tissue may be the consequence of transcriptional feedback regulation of the Lpin1 gene due to impaired lipin function. Consistent with impaired adipocyte development in fld mice, lipin mRNA expression was induced upon differentiation of 3T3-L1 preadipocytes (FIG. 3*c*) co-incident with expression of adipsin, a marker of mature adipocytes (Ailhaud et al. (1992) *Ann. Rev. Nutr.* 12: 207–233).

Lpin1 encodes a novel gene product of 891 amino acids with no similarity to previously characterized proteins or protein domains, although motif searches revealed the presence of a putative nuclear localization signal (NLS) (FIG. 4*a*). Subcellular localization of a lipin-GFP fusion protein confirmed that lipin is a nuclear protein (FIG. 4*b*).

Database searches identified several mouse and human EST and genomic sequences with significant similarities to Lpin1. Using RACE cloning and gene prediction, we identified two Lpin1-related mouse genes, Lpin2 and Lpin3, and three human homologs indicating that Lpins form a gene family in both organisms (FIG. 4*a*). The mouse and human genes form three orthologous pairs as determined by sequence comparison and genomic mapping (FIG. 4*c*). Multiple sequence alignment of lipin-related proteins revealed two strongly conserved regions, which we designate N-terminal and C-terminal lipin (NLIP and CLIP) domains (FIG. 4*a* and *d*). In addition to mouse and human proteins, we recognized several predicted proteins with NLIP and CLIP domains from a broad range of eukaryotic organisms (FIG. 4*a*), indicating that these protein domains may be required for the function of lipin and its homologs.

The identification of lipin has revealed a new factor required for normal adipose tissue development and metabolism. Elucidation of the molecular function of lipin will likely lead to new insights into these processes. The existence of at least two additional Lpin1-related genes suggests that members of this novel protein family may have roles in diverse tissues and cellular processes. The human ortholog of the Lpin1 gene, LPIN1, is a potential candidate gene for lipodystrophy, a heterogeneous group of disorders with unknown genetic determinants, except for the LMNA gene responsible for Dunnigan-type familial partial lipodystrophy (Cao and Hegele (2000) *Hum. Mol. Genet.* 9: 109–112; Shackleton et al. (2000) *Nature Genet.* 24: 153–156). Studies showing linkage of the chromosome 2p21 region harboring LPIN1 to fat mass (Comuzzie et al. (1997) *Nature Genet.* 15: 273–275) and serum leptin levels (Comuzzie et al. (1997) *Nature Genet.* 15: 273–275; Rotimi et al. (1999) *Diabetes* 48: 643–644; Hager et al. (1998) *Nature Genet.* 20: 304–308) support this possibility.

Methods

Mice.

BALB/cByJ-+/fld and C3H/HeJ-+/fld$^{2J}$ mice were obtained from the Jackson Laboratory and bred to produce the phenotypically mutant (fld/fld, fld$^{2J}$/fld$^{2J}$) and wild-type (+/+ and +/fld, +/fld$^{2J}$) mice used in these studies. Mice were fed a standard laboratory chow diet (Purina 5001) and maintained in a 14:10-hr light-dark cycle. All animal experiments were performed according to guidelines established in the "Guide for the Care and Use of Laboratory Animals".

Adipose Tissue and Leptin Analysis.

Adipose tissue morphology was assessed in 4 μm sections of epididymal fat pads stained with hematoxylin and eosin. For leptin measurements, blood was drawn from the retro-orbital sinus and plasma prepared by centrifugation. Plasma leptin levels were determined with a mouse leptin RIA kit (Linco).

Southern Blots.

Mouse genomic DNA was prepared using DNAzol (Gibco/BRL) Blots containing restriction digested DNA (5 μg/lane) were hybridized to a 257-bp 5' probe corresponding to exons 2 and 3 derived from exon trapping (Peterfy et al. (1999) *Genomics* 62: 436–444), or a 225-bp 3' probe corresponding to part of the 3' UTR and generated by PCR (5'-TAC GCA GGG ACA CAT TTC CA-3', SEQ ID NO:3) and 5'-GAG AGA TGC AGC TGC GTC A-3+, SEQ ID NO:14). Hybridizations were performed at 65° C. in 0.5 M sodium phosphate, pH 7.0, 7% SDS, 1% BSA, and washed at 65° C. to a final stringency of 0.1×SSC/0.1% SDS. Hybridization signals were detected by phosphorimaging.

Northern Blots.

Total RNA was prepared from flash-frozen mouse tissues and 3T3-L1 cells using TRIzol (Gibco/BRL) and 20 μg per lane was run in 1.2% agarose/formaldehyde gels. Poly A+RNA from liver was prepared using PolyAtract reagents (Promega) and 2 μg were analyzed. Hybridizations and washes were performed as for Southern blots, except that the temperature was 63° C. The probe used for Northern blots contained sequence corresponding to nts 1–1264 of lipin cDNA (AF180471). Adipsin cDNA was kindly provided by Dr. B. Spiegelman (Spiegelman et al. (1983) *J. Biol. Chem.* 258: 10083–10089).

PCR, RACE and DNA Sequencing.

PCR amplification of genomic DNA was performed in an M/J Research PCT-200 thermocycler (1 min 94° C., 45 sec 55° C., 1–2 min 72° C.) for 30–32 cycles. Primers for amplification of the inversion breakpoints (FIG. 2*b*) were: p1, 5'-CCC TTG AGC ACG TTC ACA-3' (SEQ ID NO:15); p2, 5'-CTG ATC GTT GTC AGT CTC T-3' (SEQ ID NO:16); p3,5'-GGT TGT GGG GAG CCT GGA-3' (SEQ ID NO: 17); p4, 5'-GCC TGC TGC AGA TGC GTT-3' (SEQ ID NO:18). RAGE cloning of full length cDNAs for Lpin2 and Lpin3 was performed using liver cDNA template prepared with the Marathon cDNA Amplification Kit (Clontech). PCR products were TA-cloned into pCR2.1 (Invitrogen), and sequenced using the Amplicycle sequencing kit (Perkin Elmer) and an ABI model 373A sequencer.

Nuclear Localization Studies.

The entire coding region of the lipin cDNA was amplified from liver cDNA using the primers 5'-GCT CGA ATT CAG ACA ATG AAT TAC GTG GGG GAG CT-3' (SEQ ID NO:19) and 5'-CGT GCA GTC GAC GCT GAG GCT GAA TGC ATG TCC TGG T-3' (SEQ ID NO:20) and cloned as an EcoRI/SalI fragment into the pEGFP-NI vector (Clontech). 3T3-L1 cells were transfected using Lipofectin (Gibco/BRL). 48 hours after transfection, cells were fixed with 4% paraformaldehyde in PBS, stained with Hoechst-33258 dye, and observed with a Zeiss Axiophot fluorescence microscope.

Cell Culture.

The 3T3-L1 preadipocyte cell line (ATCC CL-173) was maintained in DMEM containing 10% fetal bovine serum (basal medium). To induce adipocyte differentiation, cells were grown to confluence (day 0) and then cultured for 3 days in differentiation medium consisting of basal medium plus insulin (10 μml), dexamethasone (2 μg/ml), and methylisobutylxanthine (0.5 mM) (Student et al. (1980) *J. Biol. Chem.* 255: 4745–4750). On days 4–7, cells were maintained in basal medium with insulin.

Radiation Hybrid Mapping.

Lpin2 and Lpin3 were mapped using a mouse-hamster radiation hybrid panel (Research Genetics) (McCarthy et al. (1997) Genome Res. 7:1153–1161). Oligonucleotide primer pairs derived from the 3'UTR of each gene were as follows: Lpin2 (5-GGC GAG ACC CAA TCC CTG A-3', SEQ ID NO:21) and 5'-GGG TCT TCC TCT GTA AGA-3', SEQ ID NO:22); Lpin3 (5'-CCT GGC TTG AGC TTG CCT T-3', SEQ ID NO:23, and 5'-CCC ACG GCA TGC ATC TTC T-3', SEQ ID NO:24).

GenBank Accession Numbers.

Lpin1, AF180470; Lpin2, AF286723; Lpin3, AF286724

Example 2

Further Evidence of the Role of Lipin in Adipogenesis

Several lines of evidence indicate that lipin is required for normal adipogenesis. These include whole animal studies and studies in isolated cells.

Lipin deficiency in fld mice is associated with a major reduction in total body fat (3–4% as compared to 18% in wild-type mice of the same strain), as well as diminished fat pad mass (10% of normal) for epididymal, inguinal (subcutaneous), and interscapular brown fat pads. What little adipose tissue is present in fld adipose tissue depots appears abnormal, with very little lipid accumulation in cells and aberrant gene expression patterns.

Lipin deficiency attenuates obesity in a genetic model of obesity (FIGS. 5A, 5B, and 5C). When the fld mutation is transferred into a genetically obese background, such as the leptin deficient ob/ob mouse strain, resulting lipin- and leptin-double mutant mice exhibit increased food intake equivalent to ob/ob mice, but fail to become obese. At 14 weeks of age, ob/ob mice reach a weigh tof 50 grams. In contrast, mice homozygous for both the ob and fld mutations weigh to only 25 grams; indistinguishable from wild-type mice.

Lipin functions at a stage distinct from expansion of the preadipocyte lineage in the maturation of adipocytes. Lipin deficient mice exhibit normal cellularity of adipose fat pads, but fail to accumulate normal amounts of lipid in cells. Thus, lipin is not required for expansion of preadipocytes, but for the maturation steps that lead to formation of normal, lipid-dilled adipocytes.

The data from transgenic mice indicate that lipin Over-expression is associated with increased fat mass. We generated a transgenic mouse strain expression lipin specifically in adipose tissue. These mice exhibited a 60% increase in epididymal fat pad mass on a wild-type genetic background and a 35% increase on an fld strain background. These results indicate that, whereas lipin deficiency leads to a lack of normal adipose tissue formation, lipin expression levels above normal can promote excess adipose tissue development. Thus, genetic variation in lipin expression levels can be associated with either increased or decreased adipose tissue mass, and modulation of lipin levels can be of utility in conditions such as lipodystrophy and obesity.

Lipin deficiency results in an inherent inability of preadipocytes to differentiate in vitro. Adipogenesis has been examined in fibroblasts isolated from 14 day fld/fld embryos compared to those isolated from wt/fld embryos. When stimulated to differentiate with hormones (insulin, dexamethasone, methylisobutylxanthine) and the PPARγ ligand rosiglitazone, the fld/fld fibroblasts exhibit reduced lipid accumulation and reduced secretion of lipoprotein lipase activity compared to wt/fld cells. Thus lipin deficiency blocks adipocyte differentiation in a cell autonomous manner.

The lipin protein sequence bears little resemblance to proteins for which function as been previously elucidated. However, there are putative functional motifs that can be identified which we have tested. We find that lipin expression and/or activity can be controlled at several levels, including subcellular localization, protein phosphorylation, and generation of mRNA splice variants that give rise to protein isoforms.

The N-LIP and acidic lipin protein domains are required for nulear localization (Figures Error! Reference source not found. and Error! Reference source not found.). Initial studies of lipin localization within the cell revealed that lipin occurs as a predominantly nuclear protein, with a small, but consistent number of cells that exhibit exclusively cytoplasmic localization. Lipin contains a putative nuclear localization signal (NLS) comprised of basic amino acids (KKRRKRRK, SEQ ID NO:25).

Figure 8:
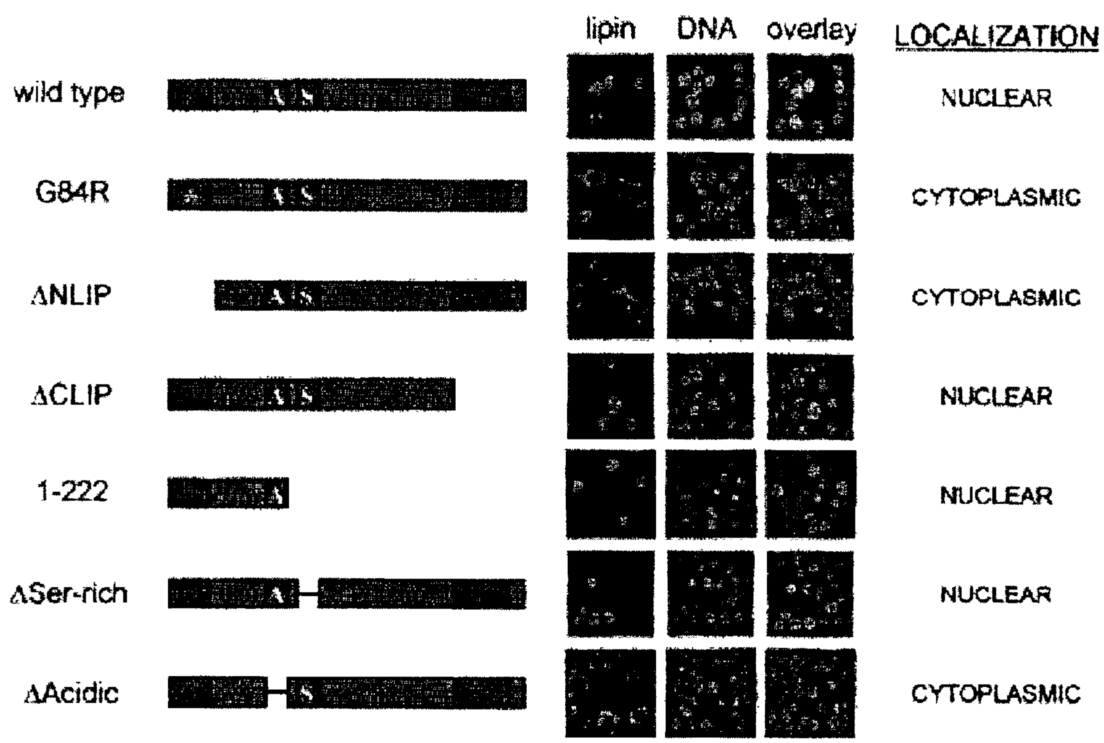
FIG. 8 illustrates the effect of various lipin mutations on the cellular localization of the mutated lipin.

Deletion mutations introduced into lipin at other sites indicate that additional lipin protein domains are also required for nuclear localization. The entire region downstream of the NLS, comprising the carboxyl-terminal 75% of the protein and containing the evolutionarily conserved C-LIP domain, is dispensible of nuclear localization. In contrast, deletion of the amino terminal 110 amino acids containing the evolutionarily conserved N-LIP domain abolishes nuclear localization. Deletion of a stretch of ~40 amino acids occurring immediately downstream from the NLS containing a high proportion of acidic amino acid residues also abolishes nuclear localization, whereas deletion of the ~40 amino acid serine-rich domain immediately following the acidic domain does not alter nuclear localization (see FIG. 8). Thus, lipin contains at least two domains (the N-LIP and acidic domains), in addition to the NLS, that are required for nuclear localization.

The lipin point mutation occurring in the fld$^{2J}$ mouse strain abolishes nuclear localization. A point mutation in lipin that leads to amino acid substitution at residue 84 (argine substituted for glycine) abolishes nuclear localization. This mutation occurs in the fld$^{2J}$ mouse strain, which shows a similar phenotype to that seen in the fld strain, suggesting that nuclear localization is required for lipin function.

Lipin gene transcription in adipocytes gives rise to two mRNA splice variants encoding lipin isoforms of potentially different functions. Lipin-1A encodes a predicted 891 amino acid protein, and lipin-1B encodes a predicted 921 amino acid protein resulting from the inclusion of an additional exon encoding 33 amino acids. The lipin-1A and -1B forms may serve different functions in the cell, as the two mRNA variants are present at similar levels in undifferentiated 353-L1 preadipocytes ,but the expression of lipin-1B increases with differentiation to levels 3-fold higher than lipin-1A after 6 days of differentiation to lipid-containing adipocytes. Furthermore, indirect immunocytochemical studies indicate that lipin-1A is localized primarily to the nucleus, while lipin-1B occurs exclusively in the cytoplasm.

Figure 7:
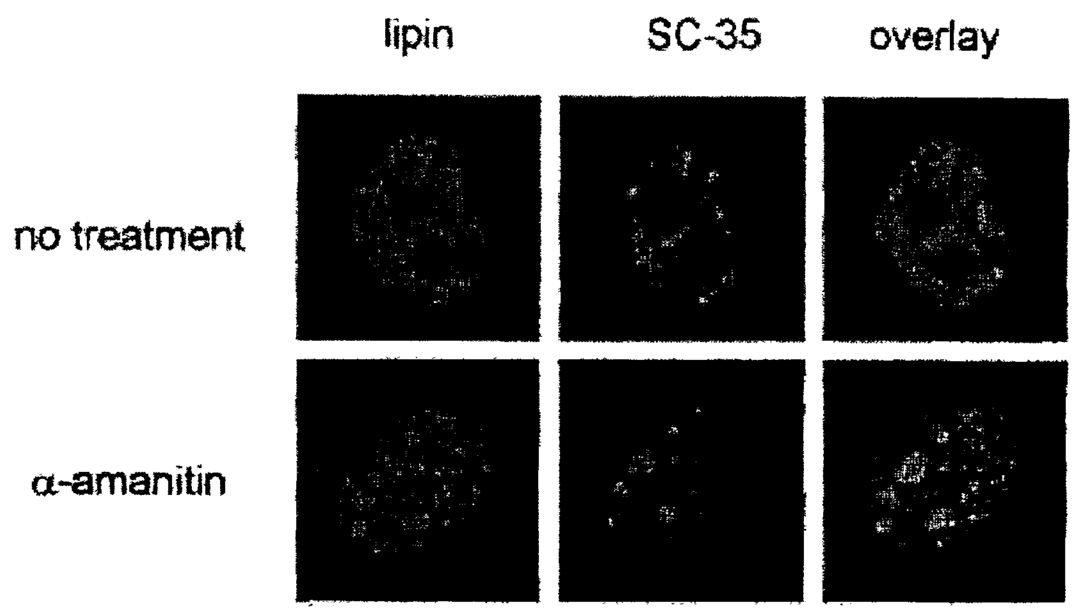
FIG. 7 illustrates that within the nucleus, lipin occurs within nuclear speckles, a compartment associated with factors involved in nuclear mRNA metabolism.

Within the nucleus, lipin occurs within nuclear speckles, a compartment associated with factors involved in nuclear mRNA metabolism (FIG. 7). Lipin that is present in the nucleus exhibits a non-homogenous distribution suggesting that it may be associated with a subnuclear compartment. It was found that when cells are treated with alpha-amanitin, an inhibitor of transcription, lipin co-localizes with SC-35 (splicing factor, 35 kD) to nuclear speckles. Nuclear speckles typically house proteins having a role in transcriptional regulation or mRNA processing and these results suggest that lipin is involved in mRNA metabolism.

Lipin is a phosphorylated protein, and the mutant fld$^{2J}$ is aberrantly phosphorylated. The lipin protein sequence contains multiple putative recognition sequences for kinase enzymes. Metabolic labeling of 3T3-L1 and 1HEK293 cells with 32P-ATP revealed that both lipin-1A and-1B become phosphorylated, resulting in labeled proteins with retarded electrophoretic mobility. Multiple phosphorylated bands are detected, suggesting that lipin contains multiple phosphorylation sites. A comparison of wild-type lipin to lipin-2J which differs at a single non-phosphorylated amino acid residue (G84R), indicates that lipin-2J is aberrantly phosphorylated as indicated by altered electrophoretic mobility and fewer phosphorylated protein species. These results suggest that the amino acid change in lipin-2J may affect phosphorylation at distant site, and in light of the exclusion of this form from the nucleus, that phosphorylation may be required for nuclear localization.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of screening for an agent that alters adipose tissue development said method comprising:

contacting a cell comprising a Lpin1 gene encoding a polypeptide comprising an NLIP domain and a CLIP domain, with a test agent; and detecting a change in the expression or activity of a Lpin1 gene product as compared to the expression or activity of a Lpin1 gene product in a cell that is contacted with the test agent at a lower concentration, where a difference in the expression or activity of said Lpin1 gene product in the contacted cell and the cell that is contacted with the lower concentration indicates that said agent alters adipose tissue development.

2. The method of claim 1, wherein said lower concentration is the absence of said test agent.

3. The method of claim 1, wherein the amount of Lpin1 gene product is detected by detecting Lpin1 mRNA in said sample.

4. The method of claim 3, wherein said level of Lpin1 mRNA is measured by hybridizing said mRNA to a probe that specifically hybridizes to a Lpin1 nucleic acid.

5. The method of claim 4, wherein said hybridizing is according to a method selected from the group consisting of a Northern blot, a Southern blot using DNA derived from the Lpin1 RNA, an array hybridization, an affinity chromatography, and an in situ hybridization.

6. The method of claim 4, wherein said probe is a member of a plurality of probes that forms an array of probes.

7. The method of claim 3, wherein the level of Lpin1 mRNA is measured using a nucleic acid amplification reaction.

8. The method of claim 1, wherein said cell is cultured ex vivo.

9. The method of claim 1, wherein said test agent is contacted to an animal comprising a cell containing the Lpin1 nucleic acid or the lipin protein.

10. A method of prescreening for an agent that alters adipose tissue development, said method comprising:

i) contacting a Lpin1 nucleic acid encoding a polypeptide comprising an NLIP domain and a CLIP domain with a test agent; and ii) detecting specific binding of said test agent to said nucleic acid.

11. The method of claim 10, further comprising recording test agents that specifically bind to said Lpin1 nucleic acid in a database of candidate agents that alter adipose tissue development.

12. The method of claim 10, wherein said test agent is not a nucleic acid.

13. The method of claim 10, wherein said binding is detected using a method selected from the group consisting of a Northern blot, a Southern blot using DNA derived from a Lpin1 RNA, an array hybridization, an affinity chromatography, and an in situ hybridization.

14. The method of claim 10, wherein said test agent is contacted directly to the Lpin1 nucleic acid.

15. The method of claim 10, wherein said test agent is contacted to a cell containing the Lpin1 nucleic acid.

16. The method of claim 15, wherein said cell is cultured ex vivo.

17. The method of claim 10, wherein said test agent is contacted to an animal comprising a cell containing the Lpin1 nucleic acid.

* * * * *

SEQUENCE LISTING

<160> NUMBER OF SEQ ID NOS: 25

<210> SEQ ID NO 1
<211> LENGTH: 5175
<212> TYPE: DNA
<213> ORGANISM: Mus musculus

<400> SEQUENCE: 1

```
cacgcgtgcg cgcctgctcg tgaatcctct tggttcagac aatgaattac gtggggcagc     60
tggccggcca ggtgtttgtg acggtgaagg agctctacaa gggactgaac cccgccacgc    120
tgtcgggatg catcgacatc attgtcatcc ggcagcccaa tggcagtctg cagtgctccc    180
ctttccacgt ccgcttcggc aagatgggtg tcctccgctc ccgagagaaa gtggtggaca    240
tagaaatcaa tggggagtcc gtggatttgc acatgaagtt gggagacaac ggagaagcat    300
tttttgttca agagactgac aacgatcagg aaatcatccc catgtacctg gccacgtccc    360
ccatcctgtc agaaggagct gcgagaatgg aaagccagct gaagaggaac tctgtggaca    420
gaatcaggtg cctggatccc actacagctg cccagggcct gcctcccagc gacaccccat    480
ccactggttc tctggggaag aagagaagga aaaggaggag gaaggcccag ttggacaatc    540
tcaaaagaga tgacaatgtc aactcatctg aggatgagga catgtttccc atagagatga    600
gctcggatga ggacacagca ccgatggatg gaagcagaac tcttcctaat gatgtaccac    660
cattccaaga tgatattcct aaggaaaact tcccctcgat ttcaacgcac ccccagtcag    720
catcgtaccc cagttcggac agagaatggt cccccagccc cagtccttca ggttcccggc    780
cctcaacacc aaaaagtgat tctgagctgg tcagtaagtc tgcagacagg ttgacgccaa    840
agaataacct ggaaatgctc tggctgtggg gtgaattgcc acaggctgca aagtcttctt    900
ctccacacaa gatgaaagag tccagcccct tagggagccg gaagactcct gataaaatga    960
attttcaggc cattcacagc gagtcttcag atacttttag tgaccagtcg ccaacaatgg   1020
cccggggact gctcatccac cagagtaagg cccagacgga aatgcagttt gtgaacgagg   1080
aggatctcga gtccttgggg gcggcagccc caccttcacc cgtggccgaa gagctcaagg   1140
ccccatatcc caacaccgca cagtcgtcga gcaagacaga ttccccttcc aggaagaaag   1200
ataaacggag ccgacacctt ggagctgatg gtgtttatct ggacgacctc acggacatgg   1260
accctgaagt ggcagccctg tatttcccca agaatgggga tcctggtggg ctccccaaac   1320
aagccagtga caacgtagcc aggtcagcca accagtcacc acagtctgtg ggaggctcgg   1380
gcatcgacag tggtgtggag agcacctccg acagcctgag ggacctgcca tccatcgcca   1440
tctccctctg cggtggcctc agtgaccaca gagagatcac caaagatgca tttttggaac   1500
aagccgtgtc atatcagcaa tttgccgaca accctgctat catcgatgac cccaacctcg   1560
tggtcaaggt tggcaataag tattacaact ggacaacagc agctcctcta cttctggcga   1620
tgcaggcttt ccagaaacct ttgccaaagg ccactgtgga atccatcatg agagataaga   1680
tgcccaaaaa gggaggaaga tggtggtttt cctggagagg aagaaatgcc acaatcaaag   1740
aggaaagcaa gcctgaacag tgcctgactg ggaaaggcca caataccgga gagcagcctg   1800
cccagcttgg cctggccacc aggataaagc atgagtcatc ctccagtgat gaagagcacg   1860
cagccgccaa gccatcaggt tcgagccacc tctctctctt gtccaacgtc agctacaaaa   1920
agaccctgcg gctcacgtcg gagcagctga aaagcttgaa gttgaagaac ggccccaatg   1980
atgtggtgtt cagtgtcact acccagtacc agggcacctg tcgctgcgag ggcaccatct   2040
```

-continued

```
acctgtggaa ttgggacgac aaagtcatca tctcagatat cgatgggacc atcacaagat   2100
ctgatactct tggtcacatt ttgcccacgc tgggaaagga ttggactcac cagggcattg   2160
caaagctgta ccacaaagta agccagaatg gmtacaagtt tctctattgt tcggcacgtg   2220
ccattgggat ggcggacatg acgaggggct acctgcactg ggtcaacgag aggggcacgg   2280
tgcttccaca gggcccgctt ctgctcagcc cgagcagcct cttctccgcc ttgcacagag   2340
aagtgattga aaagaagcca gaaaagttca aagtccagtg tttgacagac atcaagaacc   2400
tgtttttccc aaacacagaa cccttctatg ctgcttttgg gaaccggcct gctgatgtgt   2460
attcctacaa gcaagtggga gtgtccctga ataggatctt cactgtgaac cccaagggtg   2520
agctggtgca ggagcatgcc aagaccaaca tcagctcgta cgtgcggctc tgcgaagtgg   2580
tcgatcacgt cttyccattg ctaaagagaa gccattcctg tgacttcccc tgttcagaca   2640
ctttcagtaa cttcaccttt tggagagagc cactgccacc ttttgaaaac caggacatgc   2700
attcagcctc agcttgacgc gaccgagcat taaaggatag gttgtgggga ccctggagct   2760
gctgggaagg ctgatatgtg gccacctgcc taagagagaa gcatttctcc ctcggctcgc   2820
tcgctcgctc gctcgctcgc cccagggtga cacttctaag catggagggc ggagagaggc   2880
tgcatctcat cccataggct gcaagaggat tgggtgcact aggagtgtgc agacagccct   2940
ctgtttgggt ttagcacacc tcatgctgca ccctccagtc ccgtctgctc cagcaattag   3000
ttaatgtgca atacgggtga tgacccctta tcagcgggca ggccacctga gagcctgtct   3060
cagtatcact gtgcccctac cccctggaac tctgatgtgc atagggatca gtagcatcag   3120
ggacacattt ccacgacaga gacatccatg ccaccttctg cacacaggct gtgtcccgag   3180
tctaagtgaa gggaacatgg gcctcgctgg gtctcagccc tagccttggc tttgactttt   3240
tagacgttcc cttgcagtat tgccgactgt ctcactttag gtgataagct ctttaattgc   3300
tttggttaaa ggtggcctgt gacgcagctg catctctccc cattcctcat agctcaaggc   3360
tgggctattt atgccttaac gcatctgcag caggcatttc cttagcgtgc actgtctagc   3420
tctccgtaac tgcaatgcct taccttacaa gggtagtccc taaggcagcg tgtgtccgcg   3480
gcatctcagc accttctgcg tcctgctacc cagcaaggag gagccactag tgtggactca   3540
gcagcactta cgcccaccag gaaggatgcc gctaaagaca ctggttgttt tttttaaga    3600
aacatagttt ccggaagtta aattattttc tttgcagata ttatttattt ctttactgtc   3660
actgggctgc tgttgtgagc atcctagcca gatccttagg cattatagcc gtcatgaatg   3720
cattaaaagt taagtgtgat agacagtcca aagagcctca ttctgtggat gtcacactct   3780
gatcttctag aatctccgaa tcactcattt ttcttagttt tttttccccc cacagtctaa   3840
gggaaagaaa aaaaaagtaa taatttgagc aatgttcttt aagctgatag aaggttgctg   3900
tgaactgtct cagaacaatg tgaaaaatga aaagtatttt gctaaaagag ttgctttact   3960
ttgaaagtat tatttttctt aaagggtgtt ttactccaaa gacagatctt tctatttaaa   4020
tttcattgtt agggtcagag gagacaggaa caaaaaaaaa aaaaaaaaaa ggaaaagata   4080
gaaagaagag ttaaaaaaga aaaaaagcag tagaatggac tgttactctt tctgtgaaag   4140
aaaacctaga gtcactgccc ttgtagtcac tgggctctgt taaggtctca tgtggtccac   4200
atagttcaca ggaatgtaat gaaagccact gtcatctgct gtgggcgccc actgatggag   4260
aaactcggcc ctgagtgtgt ggctccctct gggagtcagg aaagccatta agctcctggc   4320
ttgttctctc gtgacctttg gaggccatgg taacccttct gccaccacgg tggttttgtg   4380
```

-continued

```
tgtattttga ttgctgtgga ctgtatacga gctcactggc ctgcagaggt tcacggccgt   4440

ctccctcatg cccaggggaa gctctggcat ctcttttcaa atgccctctg cagcccgctg   4500

tccaggtggc tccctgatgc catgttagga cttgagccag agtctctata gccaaggctg   4560

gtctacaaat gcaccatctt agacatacag cagtccttcc acctggcttg ggaacctagt   4620

tttgatatac cttaaacttc cctgtcactc taccctgaaa cagagcacac ctcccacaaa   4680

accacactct atgatctctg tgaaaatctt caggagccct gtccaggcag tgatgtggac   4740

gtctactgtt aggctccctg tgagatccaa atgagagctg caccccggtt ctctcaagtt   4800

gcttatttgc atctgcactt aaacccagag gccccaaggt cacgtgttag gatactatat   4860

gggtaccata catttcaaag ttgctcatgg aaatgagcga cttgctccat agtaacatgt   4920

cctcaaatgg cgatcccaca tgatgaagga gaacccacct ggcgcatctg agacaggctt   4980

ctgtcgtcag atactttcct tttggatttc aggttcggat cactacttca gaatatttta   5040

cttacaacgt tggctgtgtg tttgcaaatg ccggtgcgat gattaaaaaa aaaatcaata   5100

taatatttca ctgtgttgtg cttgatgcag agctagaaat ttctgtaata aacaagatgg   5160

atgaaagact tctga                                                     5175
```

<210> SEQ ID NO 2
<211> LENGTH: 5307
<212> TYPE: DNA
<213> ORGANISM: Homo sapiens

<400> SEQUENCE: 2

```
ccacgcgcgg cgccgctcgg tgcagaccat gaattacgtg ggcagttag ccggccaggt      60

gtttgtcacc gtgaaggagc tctacaaggg gctgaatccc gccacactct cagggtgcat    120

tgacatcatt gtcatccgcc agcccaatgg aaacctccaa tgctcccctt tccacgtccg    180

ctttgggaag atgggggtcc tgcgctcccg agagaaagtg gttgacatag aaatcaatgg    240

ggaatctgtg gatttgcata tgaaattggg agataatgga gaagcatttt ttgttcaaga    300

aacagataat gatcaggaag ttatccctat gcacctggcc acctccccca tcctgtcaga    360

aggagcttcg agaatggaat gccagctgaa aaggggctct gtggacagga tgagaggcct    420

ggaccccagc acgccagccc aagtgatcgc tcccagcgag acgccgtcaa gcagctctgt    480

agtaaagaag agaagaaaaa ggaggagaaa gtcacagctg gacagcctga agagagatga    540

caacatgaac acatctgagg atgaggacat gttccccatc gagatgagct cggatgaggc    600

catggagctg ctggagagca gcagaactct tcctaatgat atacctccat tccaagatga    660

tattcctgag gaaaacctct ccctggctgt gatttaccct cagtcagcct catacctaa     720

ttcggataga gagtggtcac ccactcccag tccttccggt tcccgacctt caacacctaa    780

aagtgattca gaattggtca gcaagtccac ggaaaggaca gggcagaaga acccagaaat    840

gctttggctg tggggagagc tgccgcaggc tgctaagtct tcttctccac acaagatgaa    900

agagtccagc ccattgagca gtagaaaaat ttgtgataaa agtcactttc aggccattca    960

cagcgaatct tcagacactt ttagtgacca atcgccaact ctggtcggtg gggcactttt   1020

ggaccagaac aagcctcaga cagaaatgca gtttgtgaat gaagaagacc tggagacctt   1080

aggagcagca gcgccactct tgcccatgat cgaggagctc aaacccccct ctgccagtgt   1140

agtccagaca gcaaacaaga cggattctcc ttccaggaaa agagataaac gaagccgaca   1200

tcttggtgct gacggcgtct acttggatga cctcacagac atggatcctg aagtggcggc   1260

cctgtatttt cccaaaaacg gagatccttc cggactcgca aaacatgcaa gcgacaacgg   1320
```

-continued

```
agcccggtca gccaaccagt ccccgcagtc ggtgggcagc tcgggcgtgg acagtggcgt   1380
ggagagcacc tcggacgggc tgagggacct cccttccatc gccatctccc tctgcggggg   1440
cctcagcgac caccgggaga tcacgaaaga tgcattcctg gagcaagctg tgtcatatca   1500
acagtttgtg gacaaccccg ctattatcga tgaccccaat ctcgtggtaa agattgggag   1560
taaatattat aactggacaa cagcagcacc cctcctcctg gcaatgcagg ccttccagaa   1620
acctttgcca aaggccactg tggaatctat catgagggat aaaatgccca aaaagggagg   1680
aagatggtgg ttttcatgga ggggaagaaa caccacaatc aaggaggaaa gtaagccaga   1740
gcagtgcttg gctggcaagg cccatagcac cggagagcaa ccgccgcagc tcagcttggc   1800
caccagggta aagcatgaat catcctccag tgatgaggag cgcgcagctg ccaagccatc   1860
aaacgcaggc cacctccctc ttctgcctaa tgtcagctac aagaagactc tccggctgac   1920
ttccgagcag cttaaaagct tgaagttgaa gaatggcccc aacgacgtgg ttttcagtgt   1980
caccacgcag taccaaggca cgtgccgctg tgagggcacc atctatctgt ggaactggga   2040
tgataaagtc atcatttctg atattgatgg gacaattacc agatcagata ctcttggcca   2100
cattttgccc acccttggga aggattggac ccatcagggc atcgctaagc tgtaccataa   2160
agtgagccag aatggatata aatttctcta ctgttctgcc cgtgccatcg ggatggcgga   2220
catgacgcgg ggctacctgc actgggtcaa cgagaggggc acggtgctgc cccaggggcc   2280
cctgctgctg agtcccagca gcctcttctc tgccctgcac agagaagtga ttgaaaagaa   2340
gccagaaaag tttaaagtcc agtgtttgac agacatcaaa aacctgtttt tccccaacac   2400
agaacccttt tatgctgctt ttggaaaccg accagctgat gtgtattcat acaagcaagt   2460
aggagtgtct ttgaatagaa tatttaccgt caaccctaaa ggagagctgg tacaggaaca   2520
tgcaaagacc aacatctctt cgtatgtgag actctgtgaa gtagtcgacc acgttttccc   2580
gttgctgaaa agaagccatt cttcagactt tccctgttcg gataccttca gtaacttcac   2640
cttttggaga gagccactgc caccttttga aaaccaggac attcattctg cctcagcgta   2700
aaatgtccca agcagcctct tgccagcagt gcagagcctg gttgtcaccc attaaaggat   2760
aggtctcccc ggagtgcaca gctccacctg ggagcctggc gcgtcatcat tggcctgaca   2820
gcagagagaa ttgagaagca tttctcccct gccccacccc ggggctgaca tttctaagca   2880
agataggaag ggagcacttt ctaggctagg agttgggtgc atttgtaccg tgaaaagcat   2940
tcctcagttg tggcttaatg ccagttacga cgctgccttt ccggcctgct ccagcaagta   3000
gctactggtt cacgtgcagt ttggggctgt gaaacctagg cagaaggcgg ctgtctgagg   3060
gctgtccccg cctaggacag ggtcaatcga ggaatgccag atgtgcacgg tttttggcaa   3120
agtagggggc acatttccat tatagcaatg ttagtgccac caccttctga acacagtggg   3180
gagggctgtg aaggctcatg tgacctggat ctgaggtctc tgatagaaat ctggacgcca   3240
ccgggtccag gcctggcctc agacttggcc ttgtggatgg gccccttaca gtatttgctg   3300
actagtctca tttttaggtg ataagttttt ctttaattcc tttggttaaa gatagtctat   3360
ttcattggca tatctccccc cagtttttgt ggctcaaggc tggaatattt atgccttaat   3420
atatctatgg cagacattta agaatgcgct ttatctagct catggtaact ttgcaacgcc   3480
ttagattaaa atgacagtaa atattactaa ggcagtattt tgaatgagtt tgacactgcc   3540
ggcttccttc catccagcga ggtggtgctg acagtgtgga cttgagcaca cttatgccaa   3600
atgataatga tactgacttc tgttgggagc tctccaaaga aactggttgg ttttaagaaa   3660
```

-continued

```
atagtttcaa gaagttcaac tatattcttt tagatattat gtattgtttt actctgatta   3720

ggttactgtg ataggcattt attcatattc tttctatacc actgtcatta atatattaaa   3780

aagatgtatg tgttagacta tcgaaagggc cttattctct ctttctcata gactgacctt   3840

cttttggaat ttctgagtca tttattttcc ttagcttttt ccactcaaat taagggcaag   3900

cgaaaaagta ataatttggc attctttaag cctacagaat gtgattcttt cacttgttta   3960

ttacactggc tcgtggacag aacaatttga aaagtgaaag aattattttg gtaaaagatt   4020

ttgctttact tttcgaagca ttattttttt aaagagtgtt ttactccaac gattgaaaca   4080

ttttcctatt taaatttcat cgttagaatc acaggaggca aaaaatggaa cggttgaatg   4140

aaattttact ctttctgtga aagaaaatcc acagagttgt tgcctccgtt gtagttggtg   4200

ggccccgtta gcattggatg cctttgccaa atggttcatg tggacacaca aaggcaaaca   4260

gatctgccat cgatcgcaga tttctgtaga aacacggatg tgcatgtgca gattcccttt   4320

tgcaggtatt aaaaataatt aaaaatagtc ctgcctgagg ttgcagtgag ccgagcttgc   4380

actactgcac tccagcctgg gtgacagagt aagactccat gtcaaaaaaa aaaaaaaaaa   4440

aaaaaagtcc tgccttaact aactcctctg cgcttgttca ctagtaacct aaagaggcta   4500

tattcattct ttatgcaatg agggtatttt tgagtgaatt ttaactgctc tgaactaagt   4560

ataagctcat gggcctgcaa aggttcagac ggtttctcct ttgcacccag gaggaacttt   4620

ggctgcgaga atggggggat gtatccctca tgcagttggc atccaggcag ccctctgcag   4680

cagcacaccc tgcaggcgga gttttcagag gatgcaattt tggatcccga attttgatgt   4740

accttaaact tccacatcac tgcaccctga aacagagcat gctttccaga aagtcacact   4800

ctcagatctg tgtcaagttc aatgtgagcc ctggcaaggc tggcatatta acacctgcct   4860

tctggcttct gaaagtgaga tttgtatatg ggctgcactc acgcatatac gagttggttt   4920

atctttgtgt acatgactat aacccagtga tgctgaggtc atgtgctgga atgctgtatt   4980

tggaccacac atttcaaagt tgccctatgg aaatgaatcc tacttagtga caagtcatca   5040

aatgtttgtc acatgtgatg aagacaaata tgtatacctg gcatagagaa aaatatatac   5100

ctggtacatt ggagaaaaat aattacactt tcaaagagaa ttccctttgc aattttatgt   5160

ttggatcacc actgtaagca cactttattt gcatttgatc tgtatttgta tatgctgatg   5220

caatgataaa aatcactgta atacttcatt gtgttgtact ggatgcaaag ctagaaaata   5280

ttgcaataaa tgagaccgat gaaagac                                       5307
```

```
<210> SEQ ID NO 3
<211> LENGTH: 890
<212> TYPE: PRT
<213> ORGANISM: Homo sapiens

<400> SEQUENCE: 3

Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Asn Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80
```

-continued

```
Gly Asp Asn Gly Glu Ala Phe Phe Val Gln Glu Thr Asp Asn Asp Gln
                85                  90                  95

Glu Val Ile Pro Met His Leu Ala Thr Ser Pro Ile Leu Ser Glu Gly
            100                 105                 110

Ala Ser Arg Met Glu Cys Gln Leu Lys Arg Gly Ser Val Asp Arg Met
        115                 120                 125

Arg Gly Leu Asp Pro Ser Thr Pro Ala Gln Val Ile Ala Pro Ser Glu
    130                 135                 140

Thr Pro Ser Ser Ser Ser Val Val Lys Lys Arg Arg Lys Arg Arg Arg
145                 150                 155                 160

Lys Ser Gln Leu Asp Ser Leu Lys Arg Asp Asp Asn Met Asn Thr Ser
                165                 170                 175

Glu Asp Glu Asp Met Phe Pro Ile Glu Met Ser Ser Asp Glu Ala Met
            180                 185                 190

Glu Leu Leu Glu Ser Ser Arg Thr Leu Pro Asn Asp Ile Pro Pro Phe
        195                 200                 205

Gln Asp Asp Ile Pro Glu Glu Asn Leu Ser Leu Ala Val Ile Tyr Pro
    210                 215                 220

Gln Ser Ala Ser Tyr Pro Asn Ser Asp Arg Glu Trp Ser Pro Thr Pro
225                 230                 235                 240

Ser Pro Ser Gly Ser Arg Pro Ser Thr Pro Lys Ser Asp Ser Glu Leu
                245                 250                 255

Val Ser Lys Ser Thr Glu Arg Thr Gly Gln Lys Asn Pro Glu Met Leu
            260                 265                 270

Trp Leu Trp Gly Glu Leu Pro Gln Ala Ala Lys Ser Ser Ser Pro His
        275                 280                 285

Lys Met Lys Glu Ser Ser Pro Leu Ser Ser Arg Lys Ile Cys Asp Lys
    290                 295                 300

Ser His Phe Gln Ala Ile His Ser Glu Ser Ser Asp Thr Phe Ser Asp
305                 310                 315                 320

Gln Ser Pro Thr Leu Val Gly Gly Ala Leu Leu Asp Gln Asn Lys Pro
                325                 330                 335

Gln Thr Glu Met Gln Phe Val Asn Glu Glu Asp Leu Glu Thr Leu Gly
            340                 345                 350

Ala Ala Ala Pro Leu Leu Pro Met Ile Glu Glu Leu Lys Pro Pro Ser
        355                 360                 365

Ala Ser Val Val Gln Thr Ala Asn Lys Thr Asp Ser Pro Ser Arg Lys
    370                 375                 380

Arg Asp Lys Arg Ser Arg His Leu Gly Ala Asp Gly Val Tyr Leu Asp
385                 390                 395                 400

Asp Leu Thr Asp Met Asp Pro Glu Val Ala Ala Leu Tyr Phe Pro Lys
                405                 410                 415

Asn Gly Asp Pro Ser Gly Leu Ala Lys His Ala Ser Asp Asn Gly Ala
            420                 425                 430

Arg Ser Ala Asn Gln Ser Pro Gln Ser Val Gly Ser Ser Gly Val Asp
        435                 440                 445

Ser Gly Val Glu Ser Thr Ser Asp Gly Leu Arg Asp Leu Pro Ser Ile
    450                 455                 460

Ala Ile Ser Leu Cys Gly Gly Leu Ser Asp His Arg Glu Ile Thr Lys
465                 470                 475                 480

Asp Ala Phe Leu Glu Gln Ala Val Ser Tyr Gln Gln Phe Val Asp Asn
                485                 490                 495

Pro Ala Ile Ile Asp Asp Pro Asn Leu Val Val Lys Ile Gly Ser Lys
```

-continued

```
        500                 505                 510

Tyr Tyr Asn Trp Thr Thr Ala Ala Pro Leu Leu Leu Ala Met Gln Ala
    515                 520                 525

Phe Gln Lys Pro Leu Pro Lys Ala Thr Val Glu Ser Ile Met Arg Asp
    530                 535                 540

Lys Met Pro Lys Lys Gly Gly Arg Trp Trp Phe Ser Trp Arg Gly Arg
545                 550                 555                 560

Asn Thr Thr Ile Lys Glu Glu Ser Lys Pro Glu Gln Cys Leu Ala Gly
                565                 570                 575

Lys Ala His Ser Thr Gly Glu Gln Pro Pro Gln Leu Ser Leu Ala Thr
            580                 585                 590

Arg Val Lys His Glu Ser Ser Ser Ser Asp Glu Glu Arg Ala Ala Ala
        595                 600                 605

Lys Pro Ser Asn Ala Gly His Leu Pro Leu Leu Pro Asn Val Ser Tyr
    610                 615                 620

Lys Lys Thr Leu Arg Leu Thr Ser Glu Gln Leu Lys Ser Leu Lys Leu
625                 630                 635                 640

Lys Asn Gly Pro Asn Asp Val Val Phe Ser Val Thr Thr Gln Tyr Gln
                645                 650                 655

Gly Thr Cys Arg Cys Glu Gly Thr Ile Tyr Leu Trp Asn Trp Asp Asp
            660                 665                 670

Lys Val Ile Ile Ser Asp Ile Asp Gly Thr Ile Thr Arg Ser Asp Thr
        675                 680                 685

Leu Gly His Ile Leu Pro Thr Leu Gly Lys Asp Trp Thr His Gln Gly
    690                 695                 700

Ile Ala Lys Leu Tyr His Lys Val Ser Gln Asn Gly Tyr Lys Phe Leu
705                 710                 715                 720

Tyr Cys Ser Ala Arg Ala Ile Gly Met Ala Asp Met Thr Arg Gly Tyr
                725                 730                 735

Leu His Trp Val Asn Glu Arg Gly Thr Val Leu Pro Gln Gly Pro Leu
            740                 745                 750

Leu Leu Ser Pro Ser Ser Leu Phe Ser Ala Leu His Arg Glu Val Ile
        755                 760                 765

Glu Lys Lys Pro Glu Lys Phe Lys Val Gln Cys Leu Thr Asp Ile Lys
    770                 775                 780

Asn Leu Phe Phe Pro Asn Thr Glu Pro Phe Tyr Ala Ala Phe Gly Asn
785                 790                 795                 800

Arg Pro Ala Asp Val Tyr Ser Tyr Lys Gln Val Gly Val Ser Leu Asn
                805                 810                 815

Arg Ile Phe Thr Val Asn Pro Lys Gly Glu Leu Val Gln Glu His Ala
            820                 825                 830

Lys Thr Asn Ile Ser Ser Tyr Val Arg Leu Cys Glu Val Val Asp His
        835                 840                 845

Val Phe Pro Leu Leu Lys Arg Ser His Ser Ser Asp Phe Pro Cys Ser
    850                 855                 860

Asp Thr Phe Ser Asn Phe Thr Phe Trp Arg Glu Pro Leu Pro Pro Phe
865                 870                 875                 880

Glu Asn Gln Asp Ile His Ser Ala Ser Ala
                885                 890


<210> SEQ ID NO 4
<211> LENGTH: 891
<212> TYPE: PRT
<213> ORGANISM: Mus musculus
```

```
<400> SEQUENCE: 4

Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Ser Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80

Gly Asp Asn Gly Glu Ala Phe Phe Val Gln Glu Thr Asp Asn Asp Gln
                85                  90                  95

Glu Ile Ile Pro Met Tyr Leu Ala Thr Ser Pro Ile Leu Ser Glu Gly
            100                 105                 110

Ala Ala Arg Met Glu Ser Gln Leu Lys Arg Asn Ser Val Asp Arg Ile
        115                 120                 125

Arg Cys Leu Asp Pro Thr Thr Ala Ala Gln Gly Leu Pro Pro Ser Asp
    130                 135                 140

Thr Pro Ser Thr Gly Ser Leu Gly Lys Lys Arg Arg Lys Arg Arg Arg
145                 150                 155                 160

Lys Ala Gln Leu Asp Asn Leu Lys Arg Asp Asp Asn Val Asn Ser Ser
                165                 170                 175

Glu Asp Glu Asp Met Phe Pro Ile Glu Met Ser Ser Asp Glu Asp Thr
            180                 185                 190

Ala Pro Met Asp Gly Ser Arg Thr Leu Pro Asn Asp Val Pro Pro Phe
        195                 200                 205

Gln Asp Asp Ile Pro Lys Glu Asn Phe Pro Ser Ile Ser Thr His Pro
    210                 215                 220

Gln Ser Ala Ser Tyr Pro Ser Ser Asp Arg Glu Trp Ser Pro Ser Pro
225                 230                 235                 240

Ser Pro Ser Gly Ser Arg Pro Ser Thr Pro Lys Ser Asp Ser Glu Leu
                245                 250                 255

Val Ser Lys Ser Ala Asp Arg Leu Thr Pro Lys Asn Asn Leu Glu Met
            260                 265                 270

Leu Trp Leu Trp Gly Glu Leu Pro Gln Ala Ala Lys Ser Ser Ser Pro
        275                 280                 285

His Lys Met Lys Glu Ser Ser Pro Leu Gly Ser Arg Lys Thr Pro Asp
    290                 295                 300

Lys Met Asn Phe Gln Ala Ile His Ser Glu Ser Ser Asp Thr Phe Ser
305                 310                 315                 320

Asp Gln Ser Pro Thr Met Ala Arg Gly Leu Leu Ile His Gln Ser Lys
                325                 330                 335

Ala Gln Thr Glu Met Gln Phe Val Asn Glu Glu Asp Leu Glu Ser Leu
            340                 345                 350

Gly Ala Ala Ala Pro Pro Ser Pro Val Ala Glu Glu Leu Lys Ala Pro
        355                 360                 365

Tyr Pro Asn Thr Ala Gln Ser Ser Ser Lys Thr Asp Ser Pro Ser Arg
    370                 375                 380

Lys Lys Asp Lys Arg Ser Arg His Leu Gly Ala Asp Gly Val Tyr Leu
385                 390                 395                 400

Asp Asp Leu Thr Asp Met Asp Pro Glu Val Ala Ala Leu Tyr Phe Pro
```

-continued

```
                405                 410                 415

Lys Asn Gly Asp Pro Gly Gly Leu Pro Lys Gln Ala Ser Asp Asn Val
            420                 425                 430

Ala Arg Ser Ala Asn Gln Ser Pro Gln Ser Val Gly Gly Ser Gly Ile
        435                 440                 445

Asp Ser Gly Val Glu Ser Thr Ser Asp Ser Leu Arg Asp Leu Pro Ser
    450                 455                 460

Ile Ala Ile Ser Leu Cys Gly Gly Leu Ser Asp His Arg Glu Ile Thr
465                 470                 475                 480

Lys Asp Ala Phe Leu Glu Gln Ala Val Ser Tyr Gln Gln Phe Ala Asp
                485                 490                 495

Asn Pro Ala Ile Ile Asp Asp Pro Asn Leu Val Val Lys Val Gly Asn
            500                 505                 510

Lys Tyr Tyr Asn Trp Thr Thr Ala Ala Pro Leu Leu Leu Ala Met Gln
        515                 520                 525

Ala Phe Gln Lys Pro Leu Pro Lys Ala Thr Val Glu Ser Ile Met Arg
    530                 535                 540

Asp Lys Met Pro Lys Lys Gly Gly Arg Trp Trp Phe Ser Trp Arg Gly
545                 550                 555                 560

Arg Asn Ala Thr Ile Lys Glu Glu Ser Lys Pro Glu Gln Cys Leu Thr
                565                 570                 575

Gly Lys Gly His Asn Thr Gly Glu Gln Pro Ala Gln Leu Gly Leu Ala
            580                 585                 590

Thr Arg Ile Lys His Glu Ser Ser Ser Ser Asp Glu Glu His Ala Ala
        595                 600                 605

Ala Lys Pro Ser Gly Ser Ser His Leu Ser Leu Leu Ser Asn Val Ser
    610                 615                 620

Tyr Lys Lys Thr Leu Arg Leu Thr Ser Glu Gln Leu Lys Ser Leu Lys
625                 630                 635                 640

Leu Lys Asn Gly Pro Asn Asp Val Val Phe Ser Val Thr Thr Gln Tyr
                645                 650                 655

Gln Gly Thr Cys Arg Cys Glu Gly Thr Ile Tyr Leu Trp Asn Trp Asp
            660                 665                 670

Asp Lys Val Ile Ile Ser Asp Ile Asp Gly Thr Ile Thr Arg Ser Asp
        675                 680                 685

Thr Leu Gly His Ile Leu Pro Thr Leu Gly Lys Asp Trp Thr His Gln
    690                 695                 700

Gly Ile Ala Lys Leu Tyr His Lys Val Ser Gln Asn Gly Tyr Lys Phe
705                 710                 715                 720

Leu Tyr Cys Ser Ala Arg Ala Ile Gly Met Ala Asp Met Thr Arg Gly
                725                 730                 735

Tyr Leu His Trp Val Asn Glu Arg Gly Thr Val Leu Pro Gln Gly Pro
            740                 745                 750

Leu Leu Leu Ser Pro Ser Ser Leu Phe Ser Ala Leu His Arg Glu Val
        755                 760                 765

Ile Glu Lys Lys Pro Glu Lys Phe Lys Val Gln Cys Leu Thr Asp Ile
    770                 775                 780

Lys Asn Leu Phe Phe Pro Asn Thr Glu Pro Phe Tyr Ala Ala Phe Gly
785                 790                 795                 800

Asn Arg Pro Ala Asp Val Tyr Ser Tyr Lys Gln Val Gly Val Ser Leu
                805                 810                 815

Asn Arg Ile Phe Thr Val Asn Pro Lys Gly Glu Leu Val Gln Glu His
            820                 825                 830
```

```
Ala Lys Thr Asn Ile Ser Ser Tyr Val Arg Leu Cys Glu Val Val Asp
        835                 840                 845

His Val Phe Pro Leu Leu Lys Arg Ser His Ser Cys Asp Phe Pro Cys
    850                 855                 860

Ser Asp Thr Phe Ser Asn Phe Thr Phe Trp Arg Glu Pro Leu Pro Pro
865                 870                 875                 880

Phe Glu Asn Gln Asp Met His Ser Ala Ser Ala
                885                 890


<210> SEQ ID NO 5
<211> LENGTH: 924
<212> TYPE: PRT
<213> ORGANISM: Mus musculus

<400> SEQUENCE: 5

Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Ser Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80

Gly Asp Asn Gly Glu Ala Phe Phe Val Gln Glu Thr Asp Asn Asp Gln
                85                  90                  95

Glu Ile Ile Pro Met Tyr Leu Ala Thr Ser Pro Ile Leu Ser Glu Gly
            100                 105                 110

Ala Ala Arg Met Glu Ser Gln Leu Lys Arg Asn Ser Val Asp Arg Ile
        115                 120                 125

Arg Cys Leu Asp Pro Thr Thr Ala Ala Gln Gly Leu Pro Pro Ser Asp
    130                 135                 140

Thr Pro Ser Thr Gly Ser Leu Gly Lys Lys Arg Arg Lys Arg Arg Arg
145                 150                 155                 160

Lys Ala Gln Leu Asp Asn Leu Lys Arg Asp Asp Asn Val Asn Ser Ser
                165                 170                 175

Glu Asp Glu Asp Met Phe Pro Ile Glu Met Ser Ser Asp Glu Asp Thr
            180                 185                 190

Ala Pro Met Asp Gly Ser Arg Thr Leu Pro Asn Asp Val Pro Pro Phe
        195                 200                 205

Gln Asp Asp Ile Pro Lys Glu Asn Phe Pro Ser Ile Ser Thr His Pro
    210                 215                 220

Gln Ser Ala Ser Tyr Pro Ser Ser Asp Arg Glu Trp Ser Pro Ser Pro
225                 230                 235                 240

Ser Ser Leu Val Asp Cys Gln Arg Thr Pro Pro His Leu Ala Glu Gly
                245                 250                 255

Val Leu Ser Ser Ser Cys Pro Leu Gln Ser Cys His Phe His Ala Ser
            260                 265                 270

Glu Ser Pro Ser Gly Ser Arg Pro Ser Thr Pro Lys Ser Asp Ser Glu
        275                 280                 285

Leu Val Ser Lys Ser Ala Asp Arg Leu Thr Pro Lys Asn Asn Leu Glu
    290                 295                 300

Met Leu Trp Leu Trp Gly Glu Leu Pro Gln Ala Ala Lys Ser Ser Ser
```

-continued

```
305                 310                 315                 320

Pro His Lys Met Lys Glu Ser Ser Pro Leu Gly Ser Arg Lys Thr Pro
                325                 330                 335

Asp Lys Met Asn Phe Gln Ala Ile His Ser Glu Ser Ser Asp Thr Phe
            340                 345                 350

Ser Asp Gln Ser Pro Thr Met Ala Arg Gly Leu Leu Ile His Gln Ser
        355                 360                 365

Lys Ala Gln Thr Glu Met Gln Phe Val Asn Glu Glu Asp Leu Glu Ser
    370                 375                 380

Leu Gly Ala Ala Ala Pro Pro Ser Pro Val Ala Glu Glu Leu Lys Ala
385                 390                 395                 400

Pro Tyr Pro Asn Thr Ala Gln Ser Ser Ser Lys Thr Asp Ser Pro Ser
                405                 410                 415

Arg Lys Lys Asp Lys Arg Ser Arg His Leu Gly Ala Asp Gly Val Tyr
            420                 425                 430

Leu Asp Asp Leu Thr Asp Met Asp Pro Glu Val Ala Ala Leu Tyr Phe
        435                 440                 445

Pro Lys Asn Gly Asp Pro Gly Gly Leu Pro Lys Gln Ala Ser Asp Asn
    450                 455                 460

Val Ala Arg Ser Ala Asn Gln Ser Pro Gln Ser Val Gly Gly Ser Gly
465                 470                 475                 480

Ile Asp Ser Gly Val Glu Ser Thr Ser Asp Ser Leu Arg Asp Leu Pro
                485                 490                 495

Ser Ile Ala Ile Ser Leu Cys Gly Gly Leu Ser Asp His Arg Glu Ile
            500                 505                 510

Thr Lys Asp Ala Phe Leu Glu Gln Ala Val Ser Tyr Gln Gln Phe Ala
        515                 520                 525

Asp Asn Pro Ala Ile Ile Asp Asp Pro Asn Leu Val Val Lys Val Gly
    530                 535                 540

Asn Lys Tyr Tyr Asn Trp Thr Thr Ala Ala Pro Leu Leu Leu Ala Met
545                 550                 555                 560

Gln Ala Phe Gln Lys Pro Leu Pro Lys Ala Thr Val Glu Ser Ile Met
                565                 570                 575

Arg Asp Lys Met Pro Lys Lys Gly Gly Arg Trp Trp Phe Ser Trp Arg
            580                 585                 590

Gly Arg Asn Ala Thr Ile Lys Glu Glu Ser Lys Pro Glu Gln Cys Leu
        595                 600                 605

Thr Gly Lys Gly His Asn Thr Gly Glu Gln Pro Ala Gln Leu Gly Leu
    610                 615                 620

Ala Thr Arg Ile Lys His Glu Ser Ser Ser Ser Asp Glu Glu His Ala
625                 630                 635                 640

Ala Ala Lys Pro Ser Gly Ser Ser His Leu Ser Leu Leu Ser Asn Val
                645                 650                 655

Ser Tyr Lys Lys Thr Leu Arg Leu Thr Ser Glu Gln Leu Lys Ser Leu
            660                 665                 670

Lys Leu Lys Asn Gly Pro Asn Asp Val Val Phe Ser Val Thr Thr Gln
        675                 680                 685

Tyr Gln Gly Thr Cys Arg Cys Glu Gly Thr Ile Tyr Leu Trp Asn Trp
    690                 695                 700

Asp Asp Lys Val Ile Ile Ser Asp Ile Asp Gly Thr Ile Thr Arg Ser
705                 710                 715                 720

Asp Thr Leu Gly His Ile Leu Pro Thr Leu Gly Lys Asp Trp Thr His
                725                 730                 735
```

-continued

```
Gln Gly Ile Ala Lys Leu Tyr His Lys Val Ser Gln Asn Gly Tyr Lys
            740                 745                 750

Phe Leu Tyr Cys Ser Ala Arg Ala Ile Gly Met Ala Asp Met Thr Arg
        755                 760                 765

Gly Tyr Leu His Trp Val Asn Glu Arg Gly Thr Val Leu Pro Gln Gly
    770                 775                 780

Pro Leu Leu Leu Ser Pro Ser Ser Leu Phe Ser Ala Leu His Arg Glu
785                 790                 795                 800

Val Ile Glu Lys Lys Pro Glu Lys Phe Lys Val Gln Cys Leu Thr Asp
                805                 810                 815

Ile Lys Asn Leu Phe Phe Pro Asn Thr Glu Pro Phe Tyr Ala Ala Phe
            820                 825                 830

Gly Asn Arg Pro Ala Asp Val Tyr Ser Tyr Lys Gln Val Gly Val Ser
        835                 840                 845

Leu Asn Arg Ile Phe Thr Val Asn Pro Lys Gly Glu Leu Val Gln Glu
    850                 855                 860

His Ala Lys Thr Asn Ile Ser Ser Tyr Val Arg Leu Cys Glu Val Val
865                 870                 875                 880

Asp His Val Phe Pro Leu Leu Lys Arg Ser His Ser Cys Asp Phe Pro
                885                 890                 895

Cys Ser Asp Thr Phe Ser Asn Phe Thr Phe Trp Arg Glu Pro Leu Pro
            900                 905                 910

Pro Phe Glu Asn Gln Asp Met His Ser Ala Ser Ala
        915                 920


<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6

cagacaatga attacgtggg gcagct                                          26


<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7

gctgaggctg aatgcatgtc ctggt                                           25


<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8

ccatgaatta cgtggggcag                                                 20


<210> SEQ ID NO 9
<211> LENGTH: 21
<212> TYPE: DNA
<213> ORGANISM: Artificial Sequence
<220> FEATURE:
```

```
<223> OTHER INFORMATION: PCR primer

<400> SEQUENCE: 9

cgctgaggca gaatgaatgt c                                                 21


<210> SEQ ID NO 10
<211> LENGTH: 86
<212> TYPE: PRT
<213> ORGANISM: Artificial Sequence
<220> FEATURE:
<223> OTHER INFORMATION: Consensus sequence
<221> NAME/KEY: misc_feature
<223> OTHER INFORMATION: Xaa is any amino acid

<400> SEQUENCE: 10

Asn Xaa Xaa Thr Leu Xaa Gly Xaa Ile Asp Xaa Xaa Val Xaa Xaa Xaa
1               5                   10                  15

Xaa Xaa Xaa Xaa Xaa Xaa Xaa Xaa Pro Phe His Val Arg Phe Gly Lys
            20                  25                  30

Xaa Xaa Xaa Xaa Xaa Xaa Xaa Xaa Lys Xaa Xaa Xaa Xaa Xaa Xaa Asn
        35                  40                  45

Xaa Xaa Xaa Xaa Xaa Xaa Xaa Met Lys Leu Xaa Asp Xaa Gly Xaa Ala
    50                  55                  60

Xaa Phe Val Xaa Xaa Xaa Xaa Xaa Xaa Xaa Xaa Xaa Xaa Xaa Pro Xaa
65                  70                  75                  80

Xaa Leu Xaa Xaa Ser Pro
                85


<210> SEQ ID NO 11
<211> LENGTH: 159
<212> TYPE: PRT
<213> ORGANISM: Artificial Sequence
<220> FEATURE:
<223> OTHER INFORMATION: Consensus sequence
<221> NAME/KEY: misc_feature
<223> OTHER INFORMATION: Xaa is any amino acid

<400> SEQUENCE: 11

Tyr Xaa Xaa Xaa Xaa Arg Leu Xaa Xaa Xaa Xaa Xaa Xaa Xaa Leu Xaa
1               5                   10                  15

Leu Xaa Xaa Gly Xaa Asn Xaa Xaa Xaa Phe Xaa Xaa Xaa Xaa Xaa Xaa
            20                  25                  30

Xaa Gly Xaa Xaa Xaa Xaa Xaa Xaa Xaa Xaa Xaa Xaa Xaa Xaa Xaa Xaa
        35                  40                  45

Xaa Xaa Xaa Xaa Xaa Ser Asp Ile Asp Gly Thr Ile Thr Xaa Ser Asp
    50                  55                  60

Xaa Leu Gly Xaa Xaa Xaa Xaa Xaa Xaa Gly Xaa Xaa Trp Xaa Xaa Xaa
65                  70                  75                  80

Gly Xaa Xaa Xaa Leu Xaa Xaa Xaa Xaa Xaa Xaa Asn Gly Tyr Xaa Xaa
                85                  90                  95

Xaa Tyr Xaa Xaa Xaa Arg Xaa Xaa Gly Xaa Xaa Xaa Xaa Thr Xaa Xaa
            100                 105                 110

Tyr Leu Xaa Xaa Xaa Xaa Xaa Xaa Xaa Xaa Xaa Leu Pro Xaa Gly Pro
        115                 120                 125

Xaa Xaa Leu Xaa Pro Xaa Xaa Xaa Xaa Xaa Ala Xaa Xaa Arg Glu Val
    130                 135                 140

Ile Xaa Xaa Xaa Pro Glu Xaa Phe Lys Xaa Xaa Xaa Leu Xaa Asp
145                 150                 155
```

-continued

<210> SEQ ID NO 12
<211> LENGTH: 14
<212> TYPE: RNA
<213> ORGANISM: Artificial Sequence
<220> FEATURE:
<223> OTHER INFORMATION: ribozyme sequence
<221> NAME/KEY: misc_feature
<222> LOCATION: (1)..(3)
<223> OTHER INFORMATION: n is a, c, t, or u
<221> NAME/KEY: misc_feature
<222> LOCATION: (9)..(14)
<223> OTHER INFORMATION: n is a, c, t, or u
<221> NAME/KEY: misc_feature
<222> LOCATION: (5)..(5)
<223> OTHER INFORMATION: n is a, c, t, or u
<221> NAME/KEY: misc_feature
<222> LOCATION: (4)..(3)
<223> OTHER INFORMATION: b is g, c, or u

<400> SEQUENCE: 12
nnnbngucnn nnnn 14

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
tacgcaggga cacatttcca 20

<210> SEQ ID NO 14
<211> LENGTH: 19
<212> TYPE: DNA
<213> ORGANISM: Artificial Sequence
<220> FEATURE:
<223> OTHER INFORMATION: PCR primer

<400> SEQUENCE: 14
gagagatgca gctgcgtca 19

<210> SEQ ID NO 15
<211> LENGTH: 18
<212> TYPE: DNA
<213> ORGANISM: Artificial Sequence
<220> FEATURE:
<223> OTHER INFORMATION: PCR primer

<400> SEQUENCE: 15
cccttgagca cgttcaca 18

<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
ctgatcgttg tcagtctct 19

<210> SEQ ID NO 17
<211> LENGTH: 18
<212> TYPE: DNA
<213> ORGANISM: Artificial Sequence
<220> FEATURE:
<223> OTHER INFORMATION: PCR primer

<400> SEQUENCE: 17
ggttgtgggg accctgga 18

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
gcctgctgca gatgcgtt 18

<210> SEQ ID NO 19
<211> LENGTH: 35
<212> TYPE: DNA
<213> ORGANISM: Artificial Sequence
<220> FEATURE:
<223> OTHER INFORMATION: PCR primer

<400> SEQUENCE: 19
gctcgaattc agacaatgaa ttacgtgggg cagct 35

<210> SEQ ID NO 20
<211> LENGTH: 37
<212> TYPE: DNA
<213> ORGANISM: Artificial Sequence
<220> FEATURE:
<223> OTHER INFORMATION: PCR primer

<400> SEQUENCE: 20
cgtgcagtcg acgctgaggc tgaatgcatg tcctggt 37

<210> SEQ ID NO 21
<211> LENGTH: 19
<212> TYPE: DNA
<213> ORGANISM: Artificial Sequence
<220> FEATURE:
<223> OTHER INFORMATION: PCR primer

<400> SEQUENCE: 21
ggcgagaccc aatccctga 19

<210> SEQ ID NO 22
<211> LENGTH: 18
<212> TYPE: DNA
<213> ORGANISM: Artificial Sequence
<220> FEATURE:
<223> OTHER INFORMATION: PCR primer

<400> SEQUENCE: 22
gggtcttcct ctgtaaga 18

<210> SEQ ID NO 23
<211> LENGTH: 19
<212> TYPE: DNA
<213> ORGANISM: Artificial Sequence
<220> FEATURE:
<223> OTHER INFORMATION: PCR primer

<400> SEQUENCE: 23
cctggcttga gcttgcctt 19

<210> SEQ ID NO 24
<211> LENGTH: 19

-continued

```
<212> TYPE: DNA
<213> ORGANISM: Artificial Sequence
<220> FEATURE:
<223> OTHER INFORMATION: PCR primer

<400> SEQUENCE: 24

cccacggcat gcatcttct                                            19


<210> SEQ ID NO 25
<211> LENGTH: 8
<212> TYPE: PRT
<213> ORGANISM: Homo sapiens

<400> SEQUENCE: 25

Lys Lys Arg Arg Lys Arg Arg Lys
1               5
```